US011787806B2

(12) United States Patent
Muratore et al.

(10) Patent No.: US 11,787,806 B2
(45) Date of Patent: Oct. 17, 2023

(54) ERGOLINE ANALOGUES

(71) Applicant: BECKLEY PSYTECH LIMITED, Oxford (GB)

(72) Inventors: Massimo Muratore, Oxford (GB); Amir Lotfi Moghaddam, Oxford (GB); Christopher Wong, Oxford (GB)

(73) Assignee: BECKLEY PSYTECH LIMITED, Oxford (GB)

( * ) Notice: Subject to any disclaimer, the term of this patent is extended or adjusted under 35 U.S.C. 154(b) by 0 days.

(21) Appl. No.: 17/932,854

(22) Filed: Sep. 16, 2022

(65) Prior Publication Data

US 2023/0167112 A1 Jun. 1, 2023

Related U.S. Application Data

(63) Continuation of application No. 17/941,506, filed on Sep. 9, 2022, which is a continuation of application No. PCT/IB2022/050355, filed on Jan. 17, 2022.

(30) Foreign Application Priority Data

Jan. 15, 2021 (GB) .................................. 2100549
May 18, 2021 (GB) .................................. 2107104
Nov. 11, 2021 (GB) .................................. 2116270

(51) Int. Cl.
| | |
|---|---|
| *C07D 471/06* | (2006.01) |
| *A61K 9/00* | (2006.01) |
| *C07D 519/00* | (2006.01) |
| *A61K 9/20* | (2006.01) |

(52) U.S. Cl.
CPC ............ *C07D 471/06* (2013.01); *A61K 9/006* (2013.01); *A61K 9/0019* (2013.01); *A61K 9/0031* (2013.01); *A61K 9/0056* (2013.01); *A61K 9/0073* (2013.01); *A61K 9/2072* (2013.01); *C07D 519/00* (2013.01)

(58) Field of Classification Search
CPC .. C07D 471/06; C07D 519/00; A61K 9/0019; A61K 9/0031; A61K 9/0056; A61K 9/006; A61K 9/0073; A61K 9/2072
USPC .......................................................... 546/250
See application file for complete search history.

(56) References Cited

U.S. PATENT DOCUMENTS 2,997,470 A 8/1961 Pioch

OTHER PUBLICATIONS

Gupta, S. P., "QSAR studies on drugs acting at the central nervous system," Chemical Reviews, vol. 89, No. 8, pp. 1765-1800 (1989).
Stoll, A. et al.,"Amide der stereoisomeren Lysergsäuren und Dihydrolysergsauren. 38. Mitteilung über Mutterkornalkaloide," Helvetica Chimica Acta., vol. 38, No. 3, pp. 421-433 (1955).
Johnson, F. et al., "Emetic activity of reduced lysergamides," Journal of Medicinal Chemistry, vol. 16, No. 5, pp. 532-537 (1973).
Halberstadt A. L. et al., "Pharmacological characterization of the LSD analogN-ethyl-N-cyclopropyl lysergamide (ECPLA)," Psychopharmacology, vol. 236, pp. 799-808 (2019).

(Continued)

*Primary Examiner* — Taylor V Oh

(74) *Attorney, Agent, or Firm* — Bookoff McAndrews, PLLC

(57) ABSTRACT

This invention relates to pharmaceutically acceptable ergoline analogues and salts thereof. In particular, though not exclusively, the invention relates to formulations and uses of the same as a medicament.

18 Claims, 5 Drawing Sheets

(56) References Cited

OTHER PUBLICATIONS

Huang X et al., "Drug discrimination and receptor binding studies of N-isopropyl lysergamide derivatives," *Pharmacology Biochemistry and Behavior*, vol. 47, No. 3, pp. 667-673 (1994).

Glässer, "Some Pharmacological Actions of D-Lysergic Acid Methyl Carbinolamide," *Nature*, vol. 189, pp. 313-314 (1961).

International Search Report and Written Opinion dated Jun. 13, 2022, in corresponding International Application No. PCT/IB2022/050355 (20 pages).

ERGOLINE ANALOGUES

CROSS-REFERENCE TO RELATED APPLICATIONS

This application is a continuation of U.S. application Ser. No. 17/941,506, filed on Sep. 9, 2022, which is a continuation of International Application No. PCT/IB2022/050355, filed on Jan. 17, 2022, each of which is incorporated by reference herein, PCT/IB2022/050355 claiming the benefit of priority to GB Application No. 2100549.1, filed on Jan. 15, 2021, GB Application No. 2107104.8, filed on May 18, 2021, and GB Application No. 2116270.6, filed on Nov. 11, 2021.

FIELD OF THE INVENTION

This invention relates to pharmaceutically acceptable ergoline analogues and salts thereof. In particular, though not exclusively, the invention relates to formulations and uses of the same as a medicament.

BACKGROUND TO THE INVENTION

Ergoline is the main structure for a class of alkaloids including the well-known lysergic acid diethylamide (LSD). The chemical formula of LSD is:

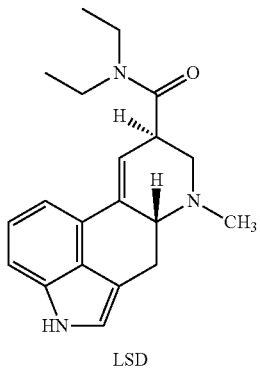

LSD

Various synthetic modifications to the structure of LSD have been made in the prior art. However, such modifications often result in a decrease in activity. Ineffective docking/binding of these compounds to the appropriate receptors may result from such structural modifications.

There remains a need in the art for ergoline analogues, and improved compositions and uses thereof.

SUMMARY

Herein disclosed is a compound of Formula (I) wherein:

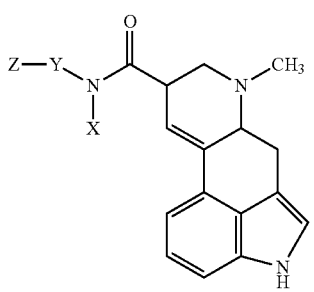

(I)

X is selected from H or $C_{1-6}$ alkyl (optionally, X is methyl or isopropyl); and Y is selected from a bond, O, CONH, NH, N($C_{1-6}$ alkyl), A-$(CH_2)_n$—B, wherein
  A is O, NH or N($C_{1-6}$ alkyl), wherein
  B is a bond, O, or NH, wherein
  n is 1 to 4; and
Z is selected from H, OH, $NH_2$, $NHC_{1-6}$ alkyl, N($C_{1-6}$ alkyl)$_2$, $C_{1-6}$ alkyl, $C_{6-10}$ aryl, $SO_2$—$C_{1-6}$ alkyl, $SO_2$—$C_{6-10}$ aryl, $C_3$-$C_{10}$ heteroaromatic or heterocyclic group comprising one, two or three heteroatoms independently selected from O and N; and
wherein X and Z are different;
or is a pharmaceutically acceptable salt thereof.

In a first aspect of the invention, there is provided compound of Formula (I) wherein:

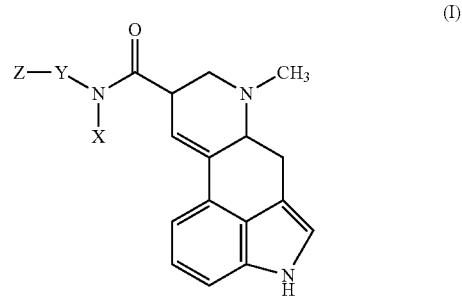

(I)

X is selected from methyl or isopropyl; and
Y is selected from a bond, O, CONH, NH, N($C_{1-6}$ alkyl), A-$(CH_2)_n$—B, wherein
  A is O, NH or N($C_{1-6}$ alkyl), wherein
  B is a bond, O, or NH, wherein
  n is 1 to 4; and
Z is selected from H, OH, $NH_2$, $NHC_{1-6}$ alkyl, N($C_{1-6}$ alkyl)$_2$, $C_{1-6}$ alkyl, $C_{6-10}$ aryl, $SO_2$—$C_{1-6}$ alkyl, $SO_2$—$C_{6-10}$ aryl, $C_3$-$C_{10}$ heteroaromatic or heterocyclic group comprising one, two or three heteroatoms independently selected from O and N; and
wherein X and Z are different;
or a pharmaceutically acceptable salt thereof.

In an embodiment the alkyl group is straight, branched or a cyclic alkyl group.

In an embodiment the alkyl group is a straight chain alkyl group. In an embodiment the alkyl group contains 1, 2 or 3 halogens.

In an embodiment X is methyl.
In an embodiment X is isopropyl.
In an embodiment Y is selected from a bond, O, CONH, NH or $NCH_3$.
In an embodiment Y is A-$(CH_2)_n$—B, wherein
  A is O or NH, wherein
  B is a bond, O or NH, wherein
  n is 1 to 4.
In an embodiment n is 2 or 3.
In an embodiment Z is selected from pyridine, morpholine, $SO_2$—$CH_3$, $SO_2$-phenyl, 8-oxa-3-azabicyclo[3.2.1]octane and 2-oxa-5-azabicyclo[2.2.1]heptane.
In an embodiment Y—Z together form the group:
  O—$(CH_2)_3$—N($CH_3$)$_2$
  NH—$(CH_2)_2$—OH
  NH—$(CH_2)_3$—OH
  NH—$(CH_2)_2$—$OCH_3$
  NH—$(CH_2)_3$—$SO_2CH_3$
  NH—$(CH_2)_2$—NH—$SO_2CH_3$, or
  O—$(CH_2)_2$—NH—$SO_2CH_3$.

In an embodiment Y—Z together form the group: NH-phenyl, pyridine, O-morpholine, NH-morpholine, NH—SO$_2$-Phenyl, NCH$_3$—SO$_2$-Phenyl, CONH-Phenyl, 8-oxa-3-azabicyclo[3.2.1]octane or 2-oxa-5-azabicyclo[2.2.1]heptane.

In an embodiment there is provided one or more compounds selected from:

| Number | IUPAC | SMILES | Structure |
|---|---|---|---|
| 001 | (1S,2R)-2-(1H-indol-3-yl)cyclopropan-1-aminium | [H]N1C([H])=C(C2=C1C([H])=C([H])C([H])=C2[H])[C@@]1([H])C([H])[C@]1([H])[N+]([H])([H])[H] | 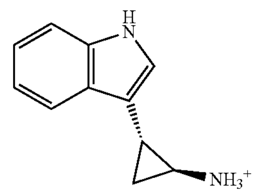 [SMILES: [NH3+][C@H]1C[C@@H]1c1c[nH]c2ccccc12] |
| 002 | (4R,6R,7R)-4-[N'-(3-hydroxypropyl)-N-methylhydrazinecarbonyl]-6-methyl-6,11-diazatetracyclo[7.6.1.0$^{2,7}$.0$^{12,16}$]hexadeca-1(16),2,9,12,14-pentaen-6-ium | [H]OC([H])([H])C([H])([H])C([H])([H])N([H])N(C(=O)[C@]1([H])C([H])=C2C3=C4C(N([H])C([H])=C4C([H])([H])[C@]2([H])[N@+]([H])(C([H])([H])[H])C1([H])[H])=C([H])C([H])=C3[H])C([H])([H])[H] | 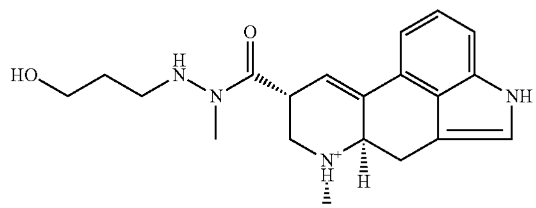 |
| 003 | (4R,6R,7R)-6-methyl-4-[methyl(pyridin-4-yl)carbamoyl]-6,11-diazatetracyclo[7.6.1.0$^{2,7}$.0$^{12,16}$]hexadeca-1(16),2,9,12,14-pentaen-6-ium | [H]N1C([H])=C2C3=C(C([H])=C([H])C([H])=C13)C1=C([H])[C@@]([H])(C(=O)N(C3=C([H])C([H])=NC([H])=C3[H])C([H])([H])[H])C([H])([H])[N@@+]([H])(C([H])([H])[H])[C@]1([H])C2([H])[H] | 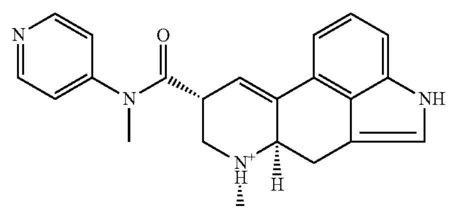 |
| 004 | (4R,6R,7R)-6-methyl-4-[N-methyl-N'-(oxan-4-yl)hydrazinecarbonyl]-6,11-diazatetracyclo[7.6.1.0$^{2,7}$.0$^{12,16}$]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+]([H])(C([H])([H])[H])C1([H])[H])=C([H])C([H])=C3[H])C([H])([H])[H])C1([H])C([H])([H])[H])C1([H])C([H])([H])C([H])([H])OC([H])([H])C1([H])[H] | 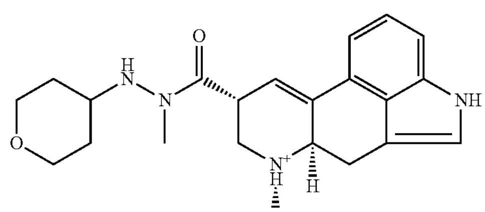 |
| 005 | (4R,6R,7R)-4-[N'-(benzenesulfonyl)-N,N'-dimethylhydrazinecarbonyl]-6-methyl-6,11-diazatetracyclo[7.6.1.0$^{2,7}$.0$^{12,16}$]hexadeca-1(16),2,9,12,14-pentaen-6-ium | [H]N1C([H])=C2C3=C(C([H])=C([H])C([H])=C13)C1=C([H])[C@@]([H])(C(=O)N(N(C([H])([H])[H])S(=O)(=O)C3=C([H])C([H])=C([H])C([H])=C([H])C3[H])C([H])([H])[H])C([H])([H])[H])[C@]1([H])C2([H])[H] | 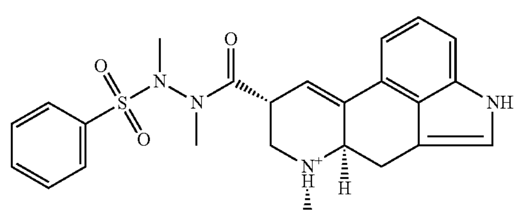 |
| 006 | (4R,6R,7R)-4-[N'-(3-methoxypropyl)-N-methylhydrazinecarbonyl]-6-methyl-6,11-diazatetracyclo[7.6.1.0$^{2,7}$.0$^{12,16}$]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+]([H])(C([H])([H])[H])C1([H])[H])=C([H])C([H])=C3[H])C([H])([H])[H])C([H])([H])C([H])([H])C([H])([H])OC([H])([H])[H] | 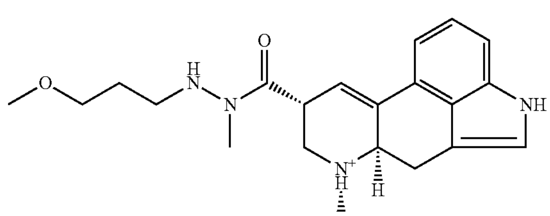 |

-continued

| Number | IUPAC | SMILES | Structure |
|---|---|---|---|
| 007 | (4R,6R,7R)-6-methyl-4-{methyl[(1R,5S)-8-oxa-3-aza-bicyclo[3.2.1]octan-3-yl]carbamoyl}-6,11-diazatetra-cyclo[7.6.1.0$^2$,$^7$.0$^{12,16}$]hexadeca-1(16),2,9,12,14-pentaen-6-ium | [H]N1C([H])=C2C3=C(C([H])=C([H])C([H])=C13)C1=C([H])[C@@]([H])(C(=O)N(N3C([H])([H])[C@@]4([H])O[C@]([H])(C([H])([H])C4([H])[H])C3([H])[H])C([H])[H])[H])C([H])([H])[N@@+]([H])(C([H])([H])[H])[C@]1([H])C2([H])[H] | 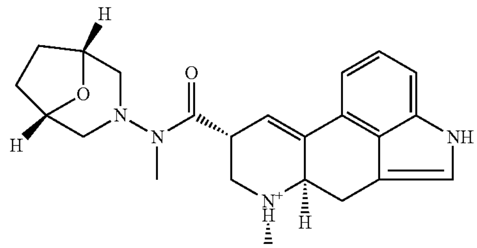 |
| 008 | (4R,6R,7R)-6-methyl-4-[methyl(oxan-4-yloxy)carbamoyl]-6,11-diazatetra-cyclo[7.6.1.0$^2$,$^7$.0$^{12,16}$]hexadeca-1(16),2,9,12,14-pentaen-6-ium | [H]N1C([H])=C2C3=C(C([H])=C([H])C([H])=C13)C1=C([H])[C@@]([H])(C(=O)N(OC3([H])C([H])([H])OC([H])([H])C3([H])[H])C([H]))[H])[H]C([H])([H])[N@@+]([H])(C([H])([H])[H])[C@]1([H])C2([H])[H] | 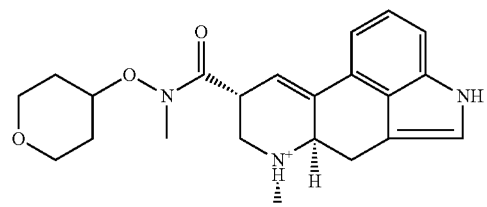 |
| 009 | (4R,6R,7R)-4-[N'-(benzenesulfonyl)-N-methylhydrazine-carbonyl]-6-methyl-6,11-diazatetra-cyclo[7.6.1.0$^2$,$^7$.0$^{12,16}$]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+]([H])(C([H])([H])[H])C1([H])[H])[H])=C([H])C([H])=C3[H])C([H])([H])[H])S(=O)(=O)C1=C([H])C([H])=C([H])C([H])=C1[H] | 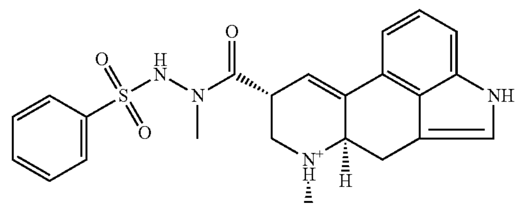 |
| 010 | (4R,6R,7R)-4-[N'-(3-methanesulfonylpropyl)-N-methylhydrazine-carbonyl]-6-methyl-6,11-diazatetra-cyclo[7.6.1.0$^2$,$^7$.0$^{12,16}$]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+]([H])(C([H])([H])[H])C1([H])[H])[H])=C([H])C([H])=C3[H]C([H])([H])[H])C)([H])([H])C([H])([H])[H])C1([H])S(=O)(=O)C([H])([H])[H] | 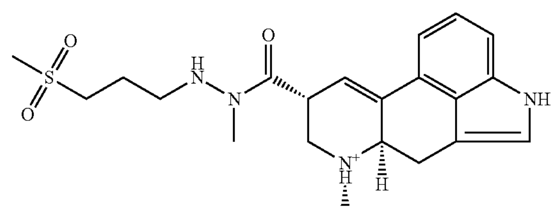 |
| 011 | (4R,6R,7R)-6-methyl-4-{[methyl(phenyl-carbamoyl)amino]carbonyl}-6,11-diazatetra-cyclo[7.6.1.0$^2$,$^7$.0$^{12,16}$]hexadeca-1(16),2,9,12,14-pentaen-6-ium | [H]N(C(=O)N(C(=O)[C@]1([H])C([H])=C2C3=C4C(N([H])C([H])=C4C([H])([H])[C@@]2([H])[N@+](HJ)(C([H])([H])[H])C1([H])[H])=C([H])C([H])=C3[H])C([H])([H])[H])C1=C([H])C([H])=C([H])C([H])=C1[H] | 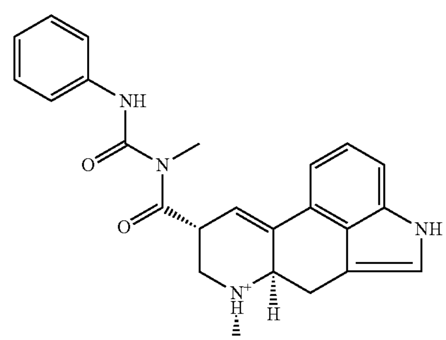 |
| 012 | (4R,6R,7R)-4-[N'-(2-methanesulfonamido-ethyl)-N-(propan-2-yl)hydrazinecarbonyl]-6-methyl-6,11-diazatetra-cyclo[7.6.1.0$^2$,$^7$.0$^{12,16}$]hexadeca-1(16),2,9,12,14-pentaen-6-ium | [H]N(N(C(=O)[C@]1([H])C([H])=C2C3=C4C(N)[H])C([H])=C4C([H])([H])[C@@]2([H])[N@+]([H])(C([H])([H])[H])C1([H])[H])=C([H])C([H])=C3[H]C([H])(C([H])([H])[H])C([H])([H])[H])C([H])([H])[H])C([H])([H])N([H])S(=O)(=O)C([H])([H])[H] | 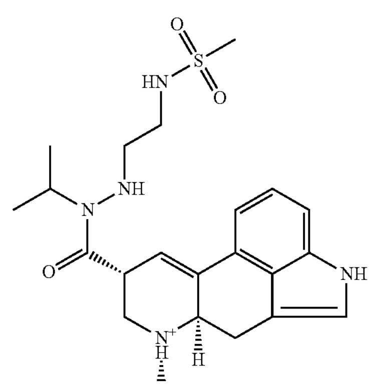 |

-continued

| Number | IUPAC | SMILES | Structure |
|---|---|---|---|
| 013 | (4R,6R,7R)-4-[N'-(2-hydroxyethyl)-N-(propan-2-yl)hydrazinecarbonyl]-6-methyl-6,11-diazatetra-cyclo[7.6.1.0², ⁷.0¹²,¹⁶]hexadeca-1(16),2,9,12,14-pentaen-6-ium | [H]OC([H])([H])C([H])) [H]N([H])N(C(=O)[C@] 1([H])C([H])=C2C3=C4 C(N([H])C([H])=C4C([H]) ([H])[C@@]2([H])[N@+] ([H])(C([H])([H])[H])C1 ([H])[H])=C([H])C([H])= C3[H])C([H])(C([H])) [H])[H])C([H])([H])[H] | 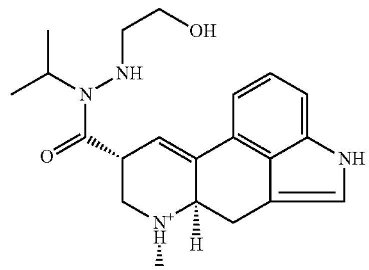 |
| 014 | (4R,6R,7R)-6-methyl-4-{[(1S,4S)-2-oxa-5-azabicyclo[2.2.1] heptan-5-yl](propan-2-yl)carbamoyl}-6,11-diazatetra-cyclo[7.6.1.0², ⁷.0¹²,¹⁶]hexadeca-1(16),2,9,12,14-pentaen-6-ium | [H]N1C([H])=C2C3=C(C ([H])=C([H])C([H])=C13) C1=C([H])[C@@]([H]) (C(=O)N(N3C([H])([H]) [C@]4([H])OC([H][H]) [C@]3[H])C4([H])[H]) C([H])(C([H])([H])[H])C ([H])([H])[H])C([H])([H]) [N@@+]([H])(C([H])) [H])[H])[C@]1([H])C2) [H])[H] | 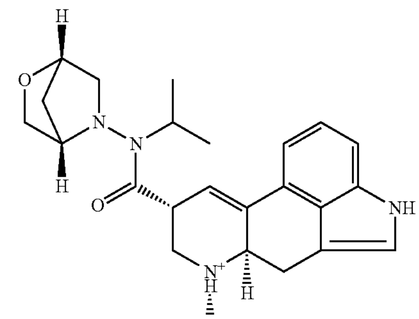 |
| 015 | (4R,6R,7R)-6-methyl-4-{[(1S,4S)-2-oxa-5-azabicyclo[2.2.2] octan-5-yl](propan-2-yl)carbamoyl}-6,11-diazatetra-cyclo[7.6.1.0², ⁷.0¹²,¹⁶]hexadeca-1(16),2,9,12,14-pentaen-6-ium | [H]N1C([H])=C2C3=C(C ([H])=C([H])C([H])=C13) C1=C([H])[C@@]([H]) (C(=O)N(N3C([H])([H]) [C@]4([H])OC([H])([H]) [C@]3[H])C([H])([H]) C4([H])[H])C([H])(C([H]) ([H])[H])C([H])([H])[H]) C([H])([H])[N@@+]([H]) (C([H])([H])[H])[C@]1 ([H])C2([H])[H] | 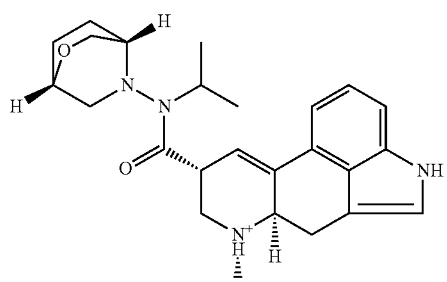 |
| 016 | (4R,6R,7R)-4-[(2-methanesulfonamido-ethoxy)(propan-2-yl)carbamoyl]-6-methyl-6,11-diazatetra-cyclo[7.6.1.0², ⁷.0¹²,¹⁶]hexadeca-1(16),2,9,12,14-pentaen-6-ium | [H]N(C([H])([H])C([H]) ([H])ON(C(=O)[C@]1([H]) C([H])=C2C3=C4C(N) [H])C([H])=C4C([H])([H]) [C@@]2([H])[N@+]) [H])(C([H])([H])[H])C1 [H])[H])=C([H])C([H])=C 3[H])C([H])(C([H])([H]) [H])C([H])([H])[H])S(=O) (=O)C([H])([H])[H] | 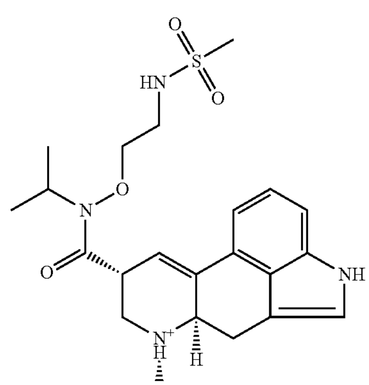 |
| 017 | (4R,6R,7R)-4-{[3-(dimethylazanium yl)propoxy](propan-2-yl)carbamoyl}-6-methyl-6,11-diazatetra-cyclo[7.6.1.0², ⁷.0¹²,¹⁶]hexadeca-1(16),2,9,12,14-pentaen-6-ium | [H]N1C([H])=C2C3=C(C ([H])=C([H])C([H])=C13) C1=C([H])[C@@]([H]) (C(=O)N(OC([H])([H])C) [H])([H])C([H])([H])[N+] ([H])(C([H])([H])[H])C) [H])([H])[H])C([H])(C([H]) ([H])[H])C([H])([H])[H]) C([H])([H])[N@@+] [H])(C([H])([H])[H])[C@] 1([H])C2([H])[H] | 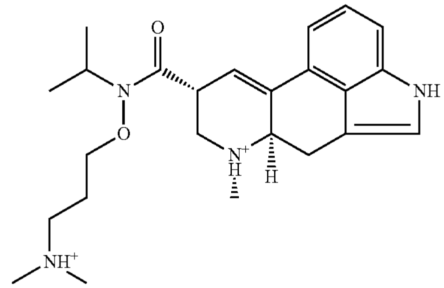 |

-continued

| Number | IUPAC | SMILES | Structure |
|---|---|---|---|
| 018 | (4R,6R,7R)-6-methyl-4-[pentyl(propan-2-yl)carbamoyl]-6,11-diazatetracyclo[7.6.1.0$^2$,$^7$.0$^{12}$,$^{16}$]hexadeca-1(16),2,9,12,14-pentaen-6-ium | [H]N1C([H])=C2C3=C(C([H])=C([H])C([H])=C13)C1=C([H])[C@@]([H])(C(=O)N(C([H])([H])C([H])([H])C([H])([H])C([H])([H])[H])C([H])([H])[H])C)[H])C([H])([H])[H])C([H])(C([H])([H])[H])C([H])([H])[H])C([H])([H])[N@@+]([H])(C([H])([H])[H])[C@]1([H])C2([H])[H] | 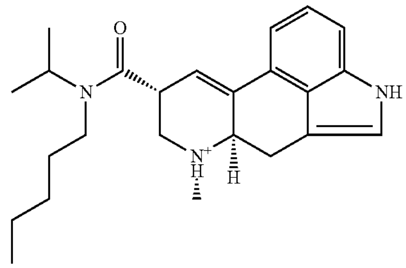 |
| 019 | (4R,6R,7R)-6-methyl-4-[(propan-2-yl)carbamoyl]-6,11-diazatetracyclo[7.6.1.0$^2$,$^7$.0$^{12}$,$^{16}$]hexadeca-1(16),2,9,12,14-pentaen-6-ium | [H]N(C(=O)[C@]1([H])C([H])=C2C3=C4C(N([H])C([H])=C4C([H])([H])[C@@]2([H])[N@+]([H])(C([H])([H])[H])C1([H])[H])=C([H])C([H])=C3[H])C([H])(C([H])([H])[H])C([H])([H])[H] | 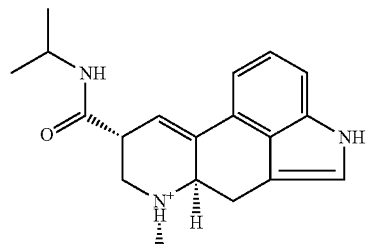 |

In an embodiment there is provided one or more compounds selected from:

| Number | Structure |
|---|---|
| 020 | 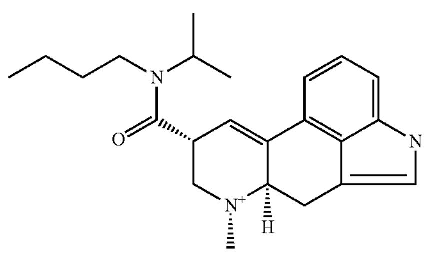 [SMILES: CCCCN(C(=O)[C@@H]1C=C2c3cccc4[nH]cc(c34)C[C@H]2[N@H+](C)C1)C(C)C] |
| 021 | 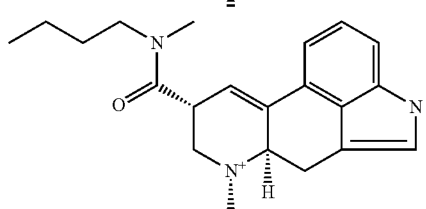 |
| 022 | 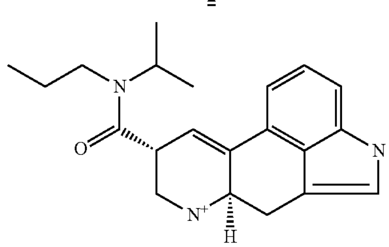 |
| 023 | 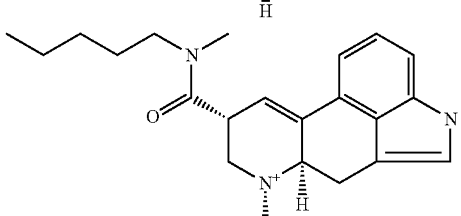 |
| 024 | |
| 025 | |

As calculated and described further herein below, compounds 001 to 019 have good 'Docking Scores' (Kcal/mol) to target the modelled receptors and are synthetically accessible. As such, compounds 001 to 019 are demonstrated to be synthetically accessible and useful as medicaments for appropriate conditions involving the target receptors, or related receptors with the associated corresponding conditions.

| Number | Synthetic Accessibility | Docking scores (Kcal/mol) |
|---|---|---|
| 001 | 2.35 | −8.579 |
| 002 | 4.39 | −13.446 |
| 003 | 4.19 | −12.761 |
| 004 | 4.55 | −12.399 |
| 005 | 4.72 | −12.957 |
| 006 | 4.51 | −12.330 |

-continued

| Number | Synthetic Accessibility | Docking scores (Kcal/mol) |
|---|---|---|
| 007 | 5.63 | −12.323 |
| 008 | 4.62 | −12.549 |
| 009 | 4.59 | −12.506 |
| 010 | 4.64 | −11.908 |
| 011 | 4.43 | −12.275 |
| 012 | 4.84 | −12.818 |
| 013 | 4.51 | −12.370 |
| 014 | 5.76 | −12.593 |
| 015 | 5.89 | −12.395 |
| 016 | 4.92 | −12.366 |
| 017 | 4.98 | −12.362 |
| 018 | 4.62 | −12.146 |
| 019 | 4.09 | −11.855 |

In an embodiment there is provided a composition comprising a pharmaceutically effective amount of a compound as described previously.

In an embodiment, the nitrogen atom on the core six-membered ring is not methylated (e.g. Compound 025 is not methylated). In an embodiment, the nitrogen atom on the core six-membered ring is methylated (e.g. Compound 025 is methylated).

In an embodiment the composition comprises a dosage amount in the range of 0.05 mg to 100 mg.

In an embodiment the composition comprises a dosage amount in the range of 0.1 mg to 50 mg.

In an embodiment the composition comprises a dosage amount in the range of 0.5 mg to 25 mg.

In an embodiment the composition comprises a dosage amount in the range of 0.5 mg to 10 mg.

In an embodiment the composition comprises a dosage amount in the range of 1 mg to 10 mg.

In an embodiment the composition comprises a dosage amount in the range of 1 mg to 8 mg.

In an embodiment the composition comprises a dosage amount in the range of 3 mg to 15 mg.

In an embodiment the composition comprises a dosage amount in the range of 0.005 mg to 100 mg.

In an embodiment the composition comprises a dosage amount in the range of 0.001 mg to 100 mg.

In an embodiment the composition comprises a dosage amount in the range of 0.0005 mg to 100 mg.

The level of the active agent can be adjusted as required by need for example to suit a certain patient group (e.g. the elderly) or the conditions being treated.

In an embodiment the composition is formulated in a dosage form selected from: oral, transdermal, inhalable, intravenous, rectal dosage, intranasal, intramuscular, or any other parenteral form.

In an embodiment the composition is formulated in a dosage form selected from: oral, transdermal, inhalable, intravenous or rectal dosage It is advantageous to be able to deliver the active agent in different forms, for example to suit a certain patient group (e.g. the elderly) or the conditions being treated.

In an embodiment the composition is formulated in a dosage form selected from: tablet, capsule, granules, powder, free-flowing powder, inhalable powder, aerosol, nebulised, vaping, buccal, sublingual, sublabial, injectable, or suppository dosage form.

In an embodiment the powder is suitable for administration by inhalation via a medicament dispenser selected from a reservoir dry powder inhaler, a unit-dose dry powder inhaler, a pre-metered multi-dose dry powder inhaler, a nasal inhaler or a pressurized metered dose inhaler.

In an embodiment the powder comprises particles, the particles having a median diameter of less than 2000 μm, 1000 μm, 5001 μm, 250 μm, 100 μm, 50 μm, or 1 μm.

In an embodiment the powder comprises particles, the particles having a median diameter of greater than 500 μm, 250 μm, 100 μm, 50 μm, 1 μm or 0.5 μm.

In an embodiment the powder comprises particles, and wherein the powder has a particle size distribution of d10=20-60 μm, and/or d50=80-120 μm, and/or d90=130-300 μm.

The nature of the powder can be adjusted to suit need. For example, if being made for nasal inhalation, then the particles may be adjusted to be much finer than if the powder is going to be formulated into a gelatine capsule, or differently again if it is going to be compacted into a tablet.

In an embodiment the compound is in the form of a salt which is amorphous or crystalline.

In an embodiment the salt is in a polymorphic crystalline form.

In an embodiment the salt is a benzoate, fumarate, citrate, acetate, succinate, halide, fluoride, chloride, bromide, iodide, oxalate, or triflate salt, optionally the salt is the chloride, benzoate or fumarate salt.

In an embodiment the salt is formulated into a composition for mucosal delivery. In an embodiment, the salt is a benzoate salt.

For the salt, the dosage amount is the equivalent amount of the free base delivered when the salt is taken. So 100 mg dosage amount may for example correspond to 117 mg of a hydrochloride salt (i.e. both providing the same molar amount of the active substance). The greater mass of the salt needed is due to the larger formula weight of the hydrogen chloride salt. Similarly, for the deuterated or triturated version of the compounds of the invention (also considered within the scope of the invention), a slight increase in mass can be expected due to the increased formula weight of these isotopic compounds.

Amorphous and crystalline substances often show different chemical/physical properties, e.g. improved rate of dissolution in a solvent, or improved thermal stability. Similarly, different polymorphs may also show different and useful chemical/physical properties.

In an embodiment the composition comprises one or more pharmaceutically acceptable carriers or excipients.

In an embodiment the composition comprises one or more of: mucoadhesive enhancer, penetrating enhancer, cationic polymers, cyclodextrins, Tight Junction Modulators, enzyme inhibitors, surfactants, chelators, and polysaccharides.

In an embodiment the composition comprises one or more of: chitosan, chitosan derivatives (such as N,N,N-trimethyl chitosan (TMC), n-propyl-(QuatPropyl), n-butyl-(Quat-Butyl) and n-hexyl (QuatHexyl)-N,N-dimethyl chitosan, chitosan chloride), β-cyclodextrin, *Clostridium perfringens* enterotoxin, zonula occludens toxin (ZOT), human neutrophil elastase inhibitor (ER143), sodium taurocholate, sodium deoxycholate sodium, sodium lauryl sulphate, glycodeoxycholat, palmitic acid, palmitoleic acid, stearic acid, oleyl acid, oleyl alcohol, capric acid sodium salt, DHA, EPA, dipalmitoyl phophatidyl choline, soybean lecithin, lysophosphatidylcholine, dodecyl maltoside, tetradecyl maltoside, EDTA, lactose, cellulose, and citric acid.

In an embodiment the compound or composition defined herein above for use in a method of treatment of a human or animal subject by therapy.

In an embodiment the method of treatment is a method of treatment of:
conditions caused by dysfunctions of the central nervous system,
conditions caused by dysfunctions of the peripheral nervous system,
conditions benefiting from sleep regulation (such as insomnia),
conditions benefiting from analgesics (such as chronic pain),
migraines,
trigeminal autonomic cephalgias (such as short-lasting unilateral neuralgiform headache with conjunctival injection and tearing (SUNCT), and short-lasting neuralgiform headaches with cranial autonomic symptoms (SUNA)),
conditions benefiting from neurogenesis (such as stroke, traumatic brain injury, Parkinson's dementia),
conditions benefiting from anti-inflammatory treatment,
depression,
anxiety,
substance use disorder,
addictive disorder,
gambling disorder,
eating disorders,
obsessive-compulsive disorders, or
body dysmorphic disorders,
optionally the condition is SUNCT and/or SUNA.

Treatment of the above conditions may be beneficially improved by taking the invention.

In an embodiment the method of treatment is a method of treatment of more than one of the above conditions, for example, the method of treatment may be a method of treatment of depression and anxiety.

In an embodiment the composition is administered one or more times a year.

In an embodiment the composition is administered one or more times a month.

In an embodiment the composition is administered one or more times a week.

In an embodiment the composition is administered one or more times a day.

In an embodiment the composition is administered at such a frequency as to avoid tachyphylaxis.

In an embodiment the composition is administered together with a complementary treatment and/or with a further active agent.

In an embodiment the further active agent is a psychedelic compound, optionally a further tryptamine.

In an embodiment the further active agent is a psychedelic compound, optionally a tryptamine.

In an embodiment the further active agent is psilocybin, psilocin or a prodrug thereof.

In an embodiment the complementary treatment is psychotherapy.

In an embodiment, there is provided a composition comprising a pharmaceutically effective amount of a compound as described herein for use in a method of treatment of treatment resistant depression.

In an embodiment, there is provided a nasal inhalation composition comprising a pharmaceutically effective amount of a compound as described herein for use in a method of treatment of treatment resistant depression.

Treatment of the above conditions may be beneficially improved by taking the invention together with some complementary treatments; also these treatments may occur much less regularly than some other treatments that require daily treatments or even multiple treatments a day.

DETAILED DESCRIPTION OF THE INVENTION

Figure 1:
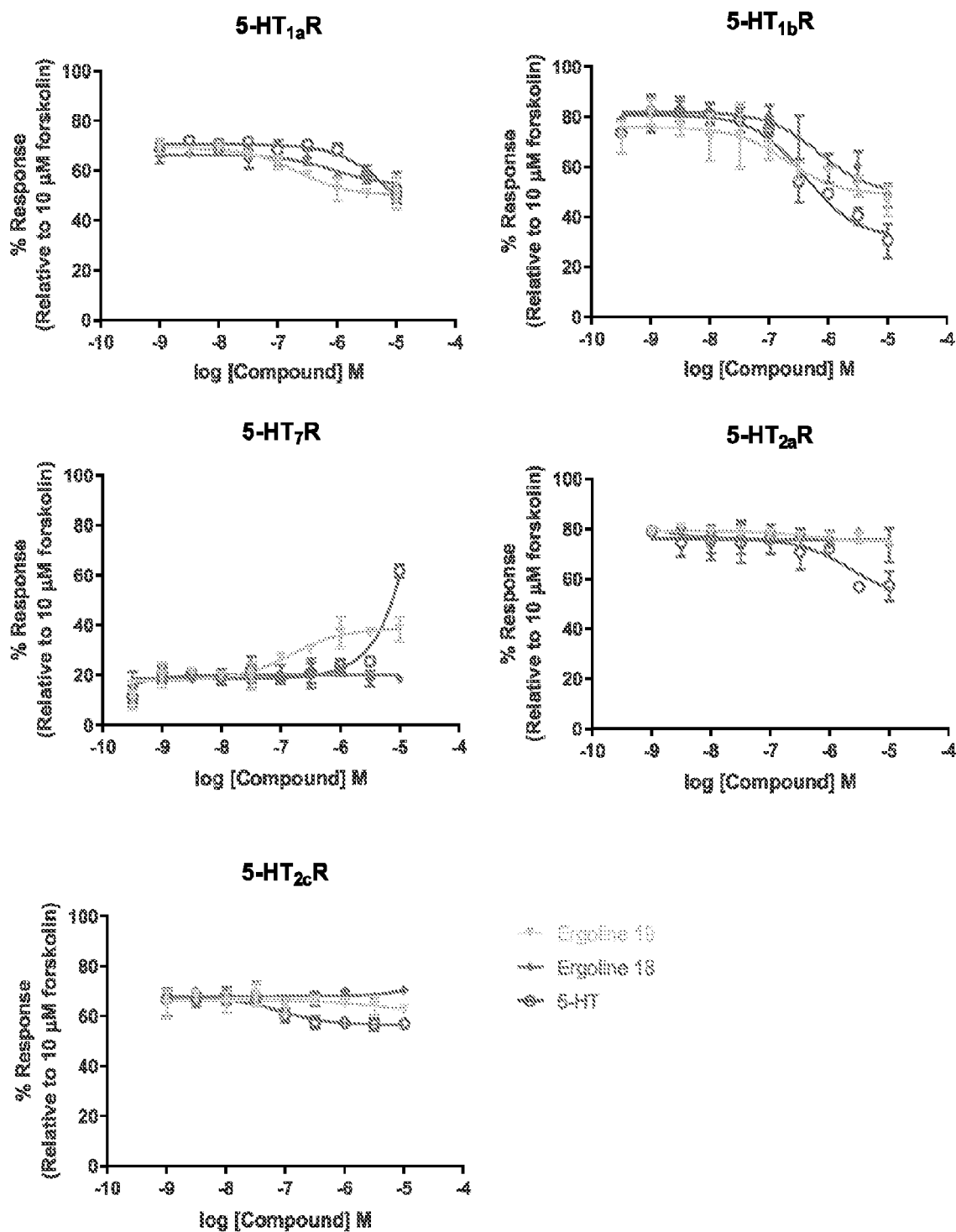
FIG. 1 shows serotonin (1a, 1b, 2a, 2c and 7 receptors) cAMP assay results for compounds 018 and 019.

The crystal structures of the serotonin receptor were retrieved from the Protein Data Bank (www.rcsb.org) [PDB ID: 5TVN and 6WGT for 5-HT2B and 5-HT2A respectively. Both proteins were prepared for docking of candidate ligands. Briefly, hydrogens were added, bond orders were assigned, and loops and side chains were filled. Restrain minimization was performed using Optimized Potentials for Liquid Simulations (OPLS2005) force field until the RMSD reached 0.3 Å from the initial geometry in order to improve steric clashes. Additionally, other possible receptor targets were used and prepared structurally as further indicated below.

Binding Pocket Analysis

Only two crystallographic structures are available from the Protein Data Bank of the 5-HT2A and 5-HT2B receptors in complex with (8alpha)-N,N-diethyl-6-methyl-9,10-didehydroergoline-8-carboxamide which represents an active isoform of LSD. The binding pockets were analysed to determine the interaction between the receptor residues and the ligands structure. Homologies modelling was applied to determine similarities in several receptor/protein targets. Moreover the binding pocket was analysed by intrinsic dynamic Domains (IDD) methodology to further verify the residues on the receptors that most contribute to the activity of the binding site.

Ligands

Initial consideration regarding anti-inflammatory properties, vaso-constriction, vaso-dilation and psychedelic effects were considered.

Upon further analysis the scaffold, lysergic acid amide deprived of the C8 amide group was used. Analysis of key attachment points was implemented and subsequently R-groups were assigned to the initial scaffold. The R-groups were selected from a library of fragments. The compounds were filtered by Lipinski's rule of five (RO5), rapid elimination of swill (REOS) and pan assay interference compounds (PAINS 1, 2, and 3).

The resulting ligand structures were prepared for docking by identifying stereoisomers with protonation states of pH7±2.

Docking

In the binding pocket residues containing hydroxyl and thiol groups were rotated to account for some flexibility of the pocket in the first stage of rigid docking. Subsequently the best compounds were used for flexible docking in order to further simulate a physiological state of the receptors.

Molecular Dynamics Simulation

Simulations for both receptors were implemented on the basis of the top ligand binding scores. All of the simulations were carried out using the MD Desmond package. Available crystal structures were used. The receptor and ligand complexes were set up in an orthorhombic box using a buffer condition of 10 Å. The orientations of the membranes (if available) were from the Orientation of Protein in Membranes (OPM) database. Ions were neutralized for the system, salt was added at a concentration of 0.15 M NaCl, and OPLS 2005 was used for the force field. Long-range electrostatic interactions were calculated with the Ewald method using a cut-off of 9 Å for Van der Waals and Coulomb interactions. The simulation was carried out in an isothermal, isobaric ensemble (NPT) with an initial temperature of 300° K and 1 bar of pressure. The temperature followed the Nose-Hoover method and the pressure was controlled by the Martyna-Tobias-Klein protocol. The simulation was set for 200 ns and trajectories were recorded every 100 ps. The default relaxation protocol for the system was used. Representative structures were extrapolated from the simulation at 0, 100, and 200 ns.

Chemical and Other Pharmacokinetic Properties

The compounds were analysed computationally regarding suitable chemical characteristic and pharmacokinetic parameters and compared across known agonists of mainly the two serotonin receptors (5-HT2A and 2B). Several algorithms were implemented.

Identified Ergoline Analogues

The structures of selected ergoline analogues are shown in the table above and further described below:

Properties of Selected Ergoline Analogues

Various properties of selected ergoline analogues are detailed in the tables below, followed by an explanation of the properties:

| Number | Formula | MW | Heavy atoms |
|---|---|---|---|
| 001 | C11H13N2 | 173.23 | 13 |
| 002 | C20H27N4O2 | 355.45 | 26 |
| 003 | C22H23N4O | 359.44 | 27 |
| 004 | C22H29N4O2 | 381.49 | 28 |
| 005 | C24H27N4O3S | 451.56 | 32 |
| 006 | C21H29N4O2 | 369.48 | 27 |
| 007 | C23H29N4O2 | 393.5 | 29 |
| 008 | C22H28N3O3 | 382.48 | 28 |
| 009 | C23H25N4O3S | 437.53 | 31 |
| 010 | C21H29N4O3S | 417.54 | 29 |
| 011 | C24H25N4O2 | 401.48 | 30 |
| 012 | C22H32N5O3S | 446.59 | 31 |
| 013 | C21H29N4O2 | 369.48 | 27 |
| 014 | C24H31N4O2 | 407.53 | 30 |
| 015 | C25H33N4O2 | 421.56 | 31 |
| 016 | C22H31N4O4S | 447.57 | 31 |
| 017 | C24H36N4O2 | 412.57 | 30 |
| 018 | C24H34N3O | 380.55 | 28 |
| 019 | C19H24N3O | 310.41 | 23 |

| Number | Aromatic heavy atoms | Csp3 | Rotatable bonds |
|---|---|---|---|
| 001 | 9 | 0.27 | 1 |
| 002 | 9 | 0.45 | 6 |
| 003 | 15 | 0.27 | 3 |
| 004 | 9 | 0.5 | 4 |
| 005 | 15 | 0.29 | 5 |
| 006 | 9 | 0.48 | 7 |
| 007 | 9 | 0.52 | 3 |
| 008 | 9 | 0.5 | 4 |
| 009 | 15 | 0.26 | 5 |
| 010 | 9 | 0.48 | 7 |
| 011 | 15 | 0.25 | 5 |
| 012 | 9 | 0.5 | 8 |
| 013 | 9 | 0.48 | 6 |
| 014 | 9 | 0.54 | 4 |
| 015 | 9 | 0.56 | 4 |
| 016 | 9 | 0.5 | 8 |
| 017 | 9 | 0.54 | 8 |
| 018 | 9 | 0.54 | 7 |
| 019 | 9 | 0.42 | 3 |

| Number | H-bond acceptors | H-bond donors | MR |
|---|---|---|---|
| 001 | 0 | 2 | 54.73 |
| 002 | 3 | 4 | 107.22 |
| 003 | 2 | 2 | 112.66 |
| 004 | 3 | 3 | 114.65 |
| 005 | 4 | 2 | 129.16 |
| 006 | 3 | 3 | 111.95 |
| 007 | 3 | 2 | 121.35 |
| 008 | 3 | 2 | 112.93 |
| 009 | 4 | 3 | 124.26 |
| 010 | 4 | 3 | 119.83 |
| 011 | 2 | 3 | 123.06 |
| 012 | 5 | 4 | 127.44 |
| 013 | 3 | 4 | 112.03 |
| 014 | 3 | 2 | 126.16 |
| 015 | 3 | 2 | 130.96 |
| 016 | 5 | 3 | 125.73 |
| 017 | 2 | 3 | 127.73 |
| 018 | 1 | 2 | 122.49 |
| 019 | 1 | 3 | 98.36 |

| Number | TPSA | LOGP | XLOGP3 |
|---|---|---|---|
| 001 | 43.43 | 1.64 | 1.36 |
| 002 | 72.8 | 2.73 | 1.65 |
| 003 | 53.43 | 2.55 | 2.7 |
| 004 | 61.8 | 2.63 | 2.39 |
| 005 | 86.3 | 3.14 | 3.26 |
| 006 | 61.8 | 3.1 | 2.19 |
| 007 | 53.01 | 3.04 | 2.7 |
| 008 | 59 | 2.88 | 2.67 |
| 009 | 95.09 | 2.59 | 3.07 |
| 010 | 95.09 | 2.61 | 1.71 |
| 011 | 69.64 | 2.85 | 3.94 |
| 012 | 107.12 | 2.16 | 1.88 |
| 013 | 72.8 | 2.85 | 2.1 |
| 014 | 53.01 | 3.15 | 3.14 |
| 015 | 53.01 | 3.05 | 3.49 |
| 016 | 104.32 | 2.28 | 2.17 |
| 017 | 54.21 | 3.9 | 3.46 |
| 018 | 40.54 | 3.46 | 4.81 |
| 019 | 49.33 | 2.71 | 2.83 |

| Number | WLOGP | MLOGP | Consensus Log P |
|---|---|---|---|
| 001 | 1.27 | −2.13 | 0.91 |
| 002 | −0.41 | −2.18 | 0.68 |
| 003 | 1.3 | −1.7 | 1.52 |
| 004 | 0.38 | −1.74 | 1.13 |
| 005 | 2.01 | −1.41 | 1.67 |
| 006 | 0.24 | −1.96 | 1.15 |
| 007 | 0.1 | −1.53 | 1.21 |
| 008 | 0.81 | −1.74 | 1.39 |
| 009 | 1.67 | −1.62 | 1.42 |
| 010 | 0.72 | −2.1 | 0.89 |
| 011 | 1.74 | −0.94 | 2.01 |
| 012 | 0.61 | −2.67 | 0.59 |
| 013 | −0.03 | −1.96 | 0.96 |
| 014 | 0.48 | −1.32 | 1.51 |
| 015 | 0.87 | −1.11 | 1.73 |
| 016 | 1.04 | −2.67 | 0.82 |
| 017 | −0.06 | −5 | 1.01 |

-continued

| Number | WLOGP | MLOGP | Consensus Log P |
|---|---|---|---|
| 018 | 2.67 | −0.49 | 2.98 |
| 019 | 0.76 | −1.58 | 1.53 |

| Number | ESOL Log S | ESOL Solubility (mg/ml) | ESOL Solubility (mol/l) |
|---|---|---|---|
| 001 | −2.22 | 1.05 | 0.00607 |
| 002 | −2.94 | 0.405 | 0.00114 |
| 003 | −3.98 | 0.0374 | 0.000104 |
| 004 | −3.68 | 0.0788 | 0.000207 |
| 005 | −4.71 | 0.0088 | 0.0000195 |
| 006 | −3.3 | 0.187 | 0.000507 |
| 007 | −4.01 | 0.0382 | 0.0000972 |
| 008 | −3.87 | 0.0519 | 0.000136 |
| 009 | −4.51 | 0.0134 | 0.0000306 |
| 010 | −3.27 | 0.222 | 0.000532 |
| 011 | −4.85 | 0.00565 | 0.0000141 |
| 012 | −3.48 | 0.148 | 0.000331 |
| 013 | −3.3 | 0.183 | 0.000496 |
| 014 | −4.3 | 0.0203 | 0.0000498 |
| 015 | −4.6 | 0.0105 | 0.0000249 |
| 016 | −3.67 | 0.0959 | 0.000214 |
| 017 | −4.27 | 0.0221 | 0.0000535 |
| 018 | −5.01 | 0.00376 | 0.00000987 |
| 019 | −3.64 | 0.0713 | 0.00023 |

| Number | Solubility Class (ESOL) | (II-method) Log S | Solubility (mg/ml) |
|---|---|---|---|
| 001 | Soluble | −1.87 | 2.31 |
| 002 | Soluble | −2.79 | 0.574 |
| 003 | Soluble | −3.48 | 0.12 |
| 004 | Soluble | −3.33 | 0.179 |
| 005 | Moderately soluble | −4.75 | 0.0081 |
| 006 | Soluble | −3.12 | 0.279 |
| 007 | Moderately soluble | −3.47 | 0.135 |
| 008 | Soluble | −3.56 | 0.105 |
| 009 | Moderately soluble | −4.73 | 0.00808 |
| 010 | Soluble | −3.32 | 0.199 |
| 011 | Moderately soluble | −5.1 | 0.00317 |
| 012 | Soluble | −3.75 | 0.0791 |
| 013 | Soluble | −3.26 | 0.203 |
| 014 | Moderately soluble | −3.92 | 0.0487 |
| 015 | Moderately soluble | −4.29 | 0.0218 |
| 016 | Soluble | −3.99 | 0.0454 |
| 017 | Moderately soluble | −4.28 | 0.0216 |
| 018 | Moderately soluble | −5.39 | 0.00154 |
| 019 | Soluble | −3.52 | 0.0929 |

| Number | Solubility (mol/l) | II method Class | Pgp substrate |
|---|---|---|---|
| 001 | 0.0134 | Very soluble | No |
| 002 | 0.00161 | Soluble | Yes |
| 003 | 0.000335 | Soluble | Yes |
| 004 | 0.000469 | Soluble | Yes |
| 005 | 0.0000179 | Moderately soluble | Yes |
| 006 | 0.000756 | Soluble | Yes |
| 007 | 0.000342 | Soluble | Yes |
| 008 | 0.000275 | Soluble | Yes |
| 009 | 0.0000185 | Moderately soluble | Yes |
| 010 | 0.000476 | Soluble | Yes |
| 011 | 0.0000079 | Moderately soluble | Yes |
| 012 | 0.000177 | Soluble | Yes |
| 013 | 0.000551 | Soluble | Yes |
| 014 | 0.000119 | Soluble | No |
| 015 | 0.0000518 | Moderately soluble | Yes |
| 016 | 0.000101 | Soluble | Yes |
| 017 | 0.0000525 | Moderately soluble | Yes |
| 018 | 0.00000404 | Moderately soluble | Yes |
| 019 | 0.000299 | Soluble | Yes |

| Number | CYP1A2 inhibitor | CYP2C19 inhibitor | CYP2C9 inhibitor |
|---|---|---|---|
| 001 | Yes | No | No |
| 002 | No | No | No |
| 003 | Yes | No | No |
| 004 | No | No | No |
| 005 | No | No | Yes |
| 006 | No | No | No |
| 007 | No | No | No |
| 008 | No | No | No |
| 009 | No | No | Yes |
| 010 | No | No | No |
| 011 | No | Yes | Yes |
| 012 | No | No | No |
| 013 | No | No | No |
| 014 | No | No | No |
| 015 | No | No | No |
| 016 | No | No | No |
| 017 | No | No | No |
| 018 | No | Yes | Yes |
| 019 | No | No | No |

| Number | CYP2D6 inhibitor | CYP3A4 inhibitor | log Kp (cm/s) |
|---|---|---|---|
| 001 | No | No | −6.39 |
| 002 | No | No | −7.3 |
| 003 | No | No | −6.58 |
| 004 | No | No | −6.93 |
| 005 | No | Yes | −6.74 |
| 006 | No | No | −7 |
| 007 | Yes | No | −6.78 |
| 008 | No | No | −6.74 |
| 009 | No | No | −6.79 |
| 010 | No | No | −7.63 |
| 011 | No | No | −5.95 |
| 012 | No | No | −7.69 |
| 013 | No | No | −7.06 |
| 014 | Yes | No | −6.56 |
| 015 | Yes | No | −6.39 |
| 016 | No | No | −7.49 |
| 017 | No | No | −6.36 |
| 018 | No | No | −5.21 |
| 019 | No | No | −6.18 |

| Number | Lipinski #violations | Ghose violations | Veber violations |
|---|---|---|---|
| 001 | 0 | 0 | 0 |
| 002 | 0 | 1 | 0 |
| 003 | 0 | 0 | 0 |
| 004 | 0 | 0 | 0 |
| 005 | 0 | 0 | 0 |
| 006 | 0 | 0 | 0 |
| 007 | 0 | 0 | 0 |
| 008 | 0 | 0 | 0 |
| 009 | 0 | 0 | 0 |
| 010 | 0 | 0 | 0 |
| 011 | 0 | 0 | 0 |
| 012 | 0 | 0 | 0 |
| 013 | 0 | 0 | 0 |
| 014 | 0 | 0 | 0 |
| 015 | 0 | 1 | 0 |
| 016 | 0 | 0 | 0 |
| 017 | 0 | 0 | 0 |

| Number | Lipinski #violations | Ghose violations | Veber violations |
|---|---|---|---|
| 018 | 0 | 0 | 0 |
| 019 | 0 | 0 | 0 |

| Number | Egan violations | Muegge violations | Bioavailability Score |
|---|---|---|---|
| 001 | 0 | 1 | 0.55 |
| 002 | 0 | 0 | 0.55 |
| 003 | 0 | 0 | 0.55 |
| 004 | 0 | 0 | 0.55 |
| 005 | 0 | 0 | 0.55 |
| 006 | 0 | 0 | 0.55 |
| 007 | 0 | 0 | 0.55 |
| 008 | 0 | 0 | 0.55 |
| 009 | 0 | 0 | 0.55 |
| 010 | 0 | 0 | 0.55 |
| 011 | 0 | 0 | 0.55 |
| 012 | 0 | 0 | 0.55 |
| 013 | 0 | 0 | 0.55 |
| 014 | 0 | 0 | 0.55 |
| 015 | 0 | 0 | 0.55 |
| 016 | 0 | 0 | 0.55 |
| 017 | 0 | 0 | 0.55 |
| 018 | 0 | 0 | 0.55 |
| 019 | 0 | 0 | 0.55 |

| Number | PAINS alerts | Brenk alerts | Leadlikeness violations |
|---|---|---|---|
| 001 | 0 | 0 | 1 |
| 002 | 0 | 0 | 1 |
| 003 | 0 | 0 | 1 |
| 004 | 0 | 0 | 1 |
| 005 | 0 | 0 | 1 |
| 006 | 0 | 0 | 1 |
| 007 | 0 | 0 | 1 |
| 008 | 0 | 1 | 1 |
| 009 | 0 | 0 | 1 |
| 010 | 0 | 0 | 1 |
| 011 | 0 | 0 | 2 |
| 012 | 0 | 0 | 2 |
| 013 | 0 | 0 | 1 |
| 014 | 0 | 0 | 1 |
| 015 | 0 | 0 | 1 |
| 016 | 0 | 1 | 2 |
| 017 | 0 | 1 | 2 |
| 018 | 0 | 0 | 2 |
| 019 | 0 | 0 | 0 |

| Number | Synthetic Accessibility | Docking scores (Kcal/mol) |
|---|---|---|
| 001 | 2.35 | −8.579 |
| 002 | 4.39 | −13.446 |
| 003 | 4.19 | −12.761 |
| 004 | 4.55 | −12.399 |
| 005 | 4.72 | −12.957 |
| 006 | 4.51 | −12.330 |
| 007 | 5.63 | −12.323 |
| 008 | 4.62 | −12.549 |
| 009 | 4.59 | −12.506 |
| 010 | 4.64 | −11.908 |
| 011 | 4.43 | −12.275 |
| 012 | 4.84 | −12.818 |
| 013 | 4.51 | −12.370 |
| 014 | 5.76 | −12.593 |
| 015 | 5.89 | −12.395 |
| 016 | 4.92 | −12.366 |
| 017 | 4.98 | −12.362 |
| 018 | 4.62 | −12.146 |
| 019 | 4.09 | −11.855 |

Naming and Strings
IUPAC name=compound name
Smile=Smile naming convention of compound
Formula=Chemical formula compound
Physiochemical Properties
MW=Molecular weight
Heavy atoms=Atoms with significantly higher atomic scattering factor than the others present
Aromatic heavy atoms=As above referring to the ring structures
Csp3=the ratio of sp3 hybridized carbons over the total carbon count of the molecule (> or equal to 0.25)
Rotable bonds=Bonds in the molecule that can rotate
H-Bonds acceptor=Bonds that can accept hydrogen ion
H-Bonds doner=Bonds that can donate hydrogen ion
MR=Molecular refractivity
TPSA=topological polar surface area
Lipophilicity
LOG P=partition coefficient for ionisable compounds. An approximation implemented by CHARMM version c36 (Chemistry at Harvard Macromolecular Mechanics)
X LOG P=another atomistic method with correction factors from: Cheng, T. et al. Computation of Octanol-Water Partition Coefficients by Guiding an Additive Model with Knowledge. J Chem Inf. Model 47, 2140-2148 (2007).
W LOG P=is another Log P using the Wildman method described in: Wildman, S. A. & Crippen, G. M. Prediction of Physicochemical Parameters by Atomic Contributions. J. Chem. Inf. Model. 39, 868-873 (1999).
M LOG P=Moriguchi topological method for partition coefficient. Moriguchi, I., Shuichi, H., Liu, Q., Nakagome, I. & Matsushita, Y. Simple Method of Calculating Octanol/Water Partition Coefficient. Chem. Pharm. Bull. 40, 127-130 (1992).
General Log p=In order to increase the accuracy of the Log P o/W the above methods were used and a general estimation of these values was condensed in "General Log P" column
Solubility
ESOL Log S=Aqueous solubility by ESOL method: Delaney, J. S. ESOL: Estimating Aqueous Solubility Directly from Molecular Structure. J. Chem. Inf. Model. 44, 1000-1005 (2004)
ESOL Solubility (mg/ml)=quantification of solubility by SwissADME
ESOL Solubility (mol/1)=as above
Solubility class for ESOL method=solubility in aqueous solution
II methods Log S=Solubility method based on: Ali, J., Camilleri, P., Brown, M. B., Hutt, A. J. & Kirton, S. B. Revisiting the general solubility equation: in silico prediction of aqueous solubility incorporating the effect of topographical polar surface area. J. Chem. Inf. Model. 52, 420-428 (2012).
Pharmacokinetics
Pgp substrate=P glycoprotein, this describes if the compound is a substrate of glycoprotein associated with the permeability of biological membranes.
The below subfamilies of the cytochrome P450 determine drug elimination and metabolism in association with Pgp data: CYP1A2 inhibitor, CYP2C19 inhibitor, CYP2C9 inhibitor, CYP2D6 inhibitor, CYP3A4 inhibitor, Drug-Likeness
Lipinski violations
Ghose violations
Veber violations
Egan violations
Muegge violations
Bioavailability Score (The Abbot Bioavailability Score)
Synthesis "PAINS (Pan-assay interference compounds)=Baell, J. B. & Holloway, G. A. New substructure filters for removal of pan assay interference compounds (PAINS) from screening libraries and for their exclusion in bioassays. J. Med. Chem. 53, 2719-2740 (2010)."

"Brenk alerts=Brenk, R. et al. Lessons learnt from assembling screening libraries for drug discovery for neglected diseases. ChemMedChem 3, 435-444 (2008)."

"Lead likeness violations=based on: Teague, S., Davis, A., Leeson, P. & Oprea, T. The Design of Lead like Combinatorial Libraries. Angew. Chem. Int. Ed. Engl. 38, 3743-3748 (1999)."

"Synthetic Accessibility=based on two papers: Fukunishi, Y., Kurosawa, T., Mikami, Y. & Nakamura, H. Prediction of synthetic accessibility based on commercially available compound databases. J Chem Inf Model 54, 3259-3267 (2014).

Ertl, P. & Schuffenhauer, A. Estimation of synthetic accessibility score of drug-like molecules based on molecular complexity and fragment contributions. J. Cheminform. 1, 8 (2009). From 1 to 10 with 1 easy and 10 complex"

Docking Scores (Kcal/mol)
Scores are reported for docking to the target, the highest negative number indicates a better binding pose of the ligand in the receptor (5-HT2A) (similar scores are related to the 5-HT2B).

Abbreviations

5-HT #=5-hydroxytryptamine receptor # HH1R=Histamine H1 receptor
A #AR=Alpha-# adrenergic receptor M.Rec=Membrane receptor
B #AR=Beta-# adrenergic receptor MAPTau=Microtubule-associated protein tau
CP450 #=Cytochrome P450 # MBLP #=Muscleblind-like protein #
CXCCRT3=C—X—C chemokine receptor type 3
Na-Dep=Sodium-dependent
D(#)DR=D(#)DR Trans.=Transporter
D(#)DR=D(#) dopamine receptor Unc=Unclassified
Enz=Enzyme where #=a number Compound/Target Data
Further Information Regarding Targets Screened
The table below details the range of targets that selected ergoline analogues were screened against and the results.

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| 001 | 5HTR2A | P28223 | HTR2A | 224 | No | 1 | 76 | 193 | M. Rec |
| | 5HTR2C | P28335 | HTR2C | 225 | No | 1 | 71 | 151 | M. Rec |
| | 5HTR2B | P41595 | HTR2B | 1833 | No | 1 | 71 | 151 | M. Rec |
| | 5HTR1A | P08908 | HTR1A | 214 | Yes | 0.74 | 12 | 528 | M. Rec |
| | 5HTR1D | P28221 | HTR1D | 1983 | No | 0.74 | 17 | 444 | M. Rec |
| | 5HTR1B | P28222 | HTR1B | 1898 | No | 0.74 | 19 | 542 | M. Rec |
| | 5HTR1E | P28566 | HTR1E | 2182 | Yes | 0.74 | 10 | 425 | M. Rec |
| | 5HTR1F | P30939 | HTR1F | 1805 | Yes | 0.74 | 10 | 425 | M. Rec |
| | 5HTR6 | P50406 | HTR6 | 3371 | No | 0.74 | 6 | 184 | M. Rec |
| | MBLP#1 | Q9NR56 | MBNL1 | 1293317 | No | 0.74 | 1 | 19 | Unc |
| | MBLP#2 | Q5VZF2 | MBNL2 | | Yes | 0.74 | 1 | 19 | Unc |
| | MBLP#3 | Q9NUKO | MBNL3 | | Yes | 0.74 | 1 | 19 | Unc |
| | Na-Dep noradrenaline Trans. | P23975 | SLC6A2 | 222 | Yes | 0.64 | 18 | 194 | Trans. |
| | Na-Dep serotonin Trans. | P31645 | SLC6A4 | 228 | No | 0.64 | 35 | 262 | Trans. |
| | Na-Dep dopamine Trans. | Q01959 | SLC6A3 | 238 | No | 0.64 | 18 | 194 | Trans. |
| 002 | D(2)DR | P14416 | DRD2 | 217 | No | 0.88 | 383 | 93 | M. Rec |
| | D(1A)DR | P21728 | DRD1 | 2056 | No | 0.88 | 33 | 20 | M. Rec |
| | D(4)DR | P21917 | DRD4 | 219 | No | 0.88 | 182 | 17 | M. Rec |
| | D(1B)DR | P21918 | DRD5 | 1850 | No | 0.88 | 27 | 20 | M. Rec |
| | 5HTR1D | P28221 | HTR1D | 1983 | No | 0.88 | 75 | 86 | M. Rec |
| | 5HTR1B | P28222 | HTR1B | 1898 | Yes | 0.88 | 225 | 111 | M. Rec |
| | 5HTR2A | P28223 | HTR2A | 224 | No | 0.88 | 166 | 34 | M. Rec |
| | 5HTR2C | P28335 | HTR2C | 225 | No | 0.88 | 111 | 23 | M. Rec |
| | D(3)DR | P35462 | DRD3 | 234 | No | 0.88 | 217 | 40 | M. Rec |
| | 5HTR2B | P41595 | HTR2B | 1833 | No | 0.88 | 111 | 23 | M. Rec |
| | 5HTR6 | P50406 | HTR6 | 3371 | No | 0.88 | 33 | 52 | M. Rec |
| | B2AR | P07550 | ADRB2 | 210 | No | 0.87 | 439 | 7 | M. Rec |
| | B1AR | P08588 | ADRB1 | 213 | No | 0.87 | 444 | 7 | M. Rec |
| | B3AR | P13945 | ADRB3 | 246 | Yes | 0.87 | 427 | 7 | M. Rec |
| | A2aAR | P08913 | ADRA2A | 1867 | No | 0.87 | 39 | 10 | M. Rec |
| 003 | D(2)DR | P14416 | DRD2 | 217 | No | 0.89 | 2724 | 112 | M. Rec |
| | D(3)DR | P35462 | DRD3 | 234 | No | 0.89 | 1579 | 46 | M. Rec |
| | 5HTR1A | P08908 | HTR1A | 214 | No | 0.87 | 1288 | 107 | M. Rec |
| | 5HTR1B | P28222 | HTR1B | 1898 | Yes | 0.87 | 1358 | 117 | M. Rec |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| | D(1A)DR | P21728 | DRD1 | 2056 | No | 0.87 | 252 | 20 | M. Rec |
| | D(1B)DR | P21918 | DRD5 | 1850 | No | 0.87 | 181 | 20 | M. Rec |
| | 5HTR1D | P28221 | HTR1D | 1983 | No | 0.86 | 549 | 86 | M. Rec |
| | 5HTR1E | P28566 | HTR1E | 2182 | No | 0.86 | 442 | 72 | M. Rec |
| | 5HTR1F | P30939 | HTR1F | 1805 | No | 0.86 | 442 | 72 | M. Rec |
| | 5HTR6 | P50406 | HTR6 | 3371 | No | 0.85 | 484 | 54 | M. Rec |
| | D(4)DR | P21917 | DRD4 | 219 | No | 0.85 | 1030 | 17 | M. Rec |
| | 5HTR2A | P28223 | HTR2A | 224 | No | 0.85 | 1067 | 35 | M. Rec |
| | 5HTR7 | P34969 | HTR7 | 3155 | No | 0.85 | 411 | 19 | M. Rec |
| | 5HTR2C | P28335 | HTR2C | 225 | No | 0.85 | 636 | 24 | M. Rec |
| | 5HTR2B | P41595 | HTR2B | 1833 | No | 0.85 | 636 | 24 | M. Rec |
| 004 | 5HTR7 | P34969 | HTR7 | 3155 | No | 0.84 | 52 | 14 | M. Rec |
| | 5HTR5A | P47898 | HTR5A | 3426 | No | 0.84 | 8 | 9 | M. Rec |
| | 5HTR6 | P50406 | HTR6 | 3371 | No | 0.84 | 65 | 39 | M. Rec |
| | D(2)DR | P14416 | DRD2 | 217 | No | 0.84 | 621 | 82 | M. Rec |
| | D(1A)DR | P21728 | DRD1 | 2056 | No | 0.84 | 48 | 19 | M. Rec |
| | D(4)DR | P21917 | DRD4 | 219 | No | 0.84 | 311 | 16 | M. Rec |
| | D(1B)DR | P21918 | DRD5 | 1850 | No | 0.84 | 40 | 19 | M. Rec |
| | 5HTR1D | P28221 | HTR1D | 1983 | No | 0.84 | 132 | 84 | M. Rec |
| | 5HTR1B | P28222 | HTR1B | 1898 | Yes | 0.84 | 342 | 99 | M. Rec |
| | 5HTR2A | P28223 | HTR2A | 224 | No | 0.84 | 285 | 32 | M. Rec |
| | 5HTR2C | P28335 | HTR2C | 225 | No | 0.84 | 217 | 21 | M. Rec |
| | D(3)DR | P35462 | DRD3 | 234 | No | 0.84 | 383 | 37 | M. Rec |
| | 5HTR2B | P41595 | HTR2B | 1833 | No | 0.84 | 217 | 21 | M. Rec |
| | 5HTR1A | P08908 | HTR1A | 214 | No | 0.83 | 333 | 89 | M. Rec |
| | A2aAR | P08913 | ADRA2A | 1867 | No | 0.81 | 75 | 9 | M. Rec |
| 005 | D(2)DR | P14416 | DRD2 | 217 | No | 0.77 | 1437 | 60 | M. Rec |
| | D(4)DR | P21917 | DRD4 | 219 | No | 0.77 | 549 | 18 | M. Rec |
| | D(3)DR | P35462 | DRD3 | 234 | No | 0.77 | 850 | 37 | M. Rec |
| | 5HTR1A | P08908 | HTR1A | 214 | No | 0.75 | 791 | 56 | M. Rec |
| | 5HTR1D | P28221 | HTR1D | 1983 | No | 0.75 | 305 | 52 | M. Rec |
| | 5HTR1B | P28222 | HTR1B | 1898 | No | 0.75 | 847 | 61 | M. Rec |
| | 5HTR2A | P28223 | HTR2A | 224 | No | 0.75 | 599 | 27 | M. Rec |
| | 5HTR1E | P28566 | HTR1E | 2182 | No | 0.75 | 236 | 45 | M. Rec |
| | 5HTR1F | P30939 | HTR1F | 1805 | No | 0.75 | 236 | 45 | M. Rec |
| | 5HTR7 | P34969 | HTR7 | 3155 | No | 0.75 | 255 | 12 | M. Rec |
| | 5HTR5A | P47898 | HTR5A | 3426 | No | 0.75 | 45 | 9 | M. Rec |
| | 5HTR6 | P50406 | HTR6 | 3371 | No | 0.75 | 417 | 87 | M. Rec |
| | 5HTR2C | P28335 | HTR2C | 225 | No | 0.75 | 368 | 15 | M. Rec |
| | 5HTR2B | P41595 | HTR2B | 1833 | No | 0.75 | 368 | 15 | M. Rec |
| | B2AR | P07550 | ADRB2 | 210 | No | 0.73 | 19 | 7 | M. Rec |
| 006 | 5HT1IA | P08908 | HTR1A | 214 | No | 0.88 | 338 | 102 | M. Rec |
| | 5HTR1B | P28222 | HTR1B | 1898 | Yes | 0.88 | 346 | 112 | M. Rec |
| | 5HTR2A | P28223 | HTR2A | 224 | No | 0.86 | 299 | 33 | M. Rec |
| | 5HTR2C | P28335 | HTR2C | 225 | No | 0.86 | 230 | 22 | M. Rec |
| | 5HTR2B | P41595 | HTR2B | 1833 | No | 0.86 | 230 | 22 | M. Rec |
| | 5HTR6 | P50406 | HTR6 | 3371 | No | 0.86 | 69 | 48 | M. Rec |
| | D(2)DR | P14416 | DRD2 | 217 | No | 0.86 | 610 | 92 | M. Rec |
| | D(1A)DR | P21728 | DRD1 | 2056 | No | 0.86 | 46 | 20 | M. Rec |
| | D(4)DR | P21917 | DRD4 | 219 | No | 0.86 | 315 | 17 | M. Rec |
| | D(1B)DR | P21918 | DRD5 | 1850 | No | 0.86 | 40 | 20 | M. Rec |
| | 5HTR1D | P28221 | HTR1D | 1983 | No | 0.86 | 131 | 85 | M. Rec |
| | 5HTR7 | P34969 | HTR7 | 3155 | No | 0.86 | 56 | 16 | M. Rec |
| | D(3)DR | P35462 | DRD3 | 234 | No | 0.86 | 377 | 38 | M. Rec |
| | B2AR | P07550 | ADRB2 | 210 | No | 0.85 | 536 | 7 | M. Rec |
| | B1AR | P08588 | ADRB1 | 213 | No | 0.85 | 539 | 7 | M. Rec |
| 007 | D(2)DR | P14416 | DRD2 | 217 | No | 0.77 | 621 | 74 | M. Rec |
| | D(1A)DR | P21728 | DRD1 | 2056 | No | 0.77 | 50 | 18 | M. Rec |
| | D(4)DR | P21917 | DRD4 | 219 | Yes | 0.77 | 334 | 15 | M. Rec |
| | D(3)DR | P35462 | DRD3 | 234 | No | 0.77 | 400 | 36 | M. Rec |
| | 5HTR6 | P50406 | HTR6 | 3371 | No | 0.75 | 65 | 26 | M. Rec |
| | 5HTR2A | P28223 | HTR2A | 224 | No | 0.75 | 309 | 26 | M. Rec |
| | D(1B)DR | P21918 | DRD5 | 1850 | No | 0.74 | 44 | 18 | M. Rec |
| | 5HTR2C | P28335 | HTR2C | 225 | No | 0.74 | 237 | 15 | M. Rec |
| | 5HTR2B | P41595 | HTR2B | 1833 | No | 0.74 | 237 | 15 | M. Rec |
| | AZaAR | P08913 | ADRA2A | 1867 | No | 0.72 | 84 | 8 | M. Rec |
| | A2BAR | P18089 | ADRA2B | 1942 | No | 0.72 | 84 | 8 | M. Rec |
| | A2CAR | P18825 | ADRA2C | 1916 | Yes | 0.72 | 84 | 8 | M. Rec |
| | MAPTau | P10636 | MAPT | 1293224 | No | 0.72 | 307 | 9 | Unc |
| | HH1R | P35367 | HRH1 | 231 | No | 0.72 | 94 | 5 | M. Rec |
| | 5HTR1D | P28221 | HTR1D | 1983 | No | 0.72 | 116 | 73 | M. Rec |
| 008 | D(2)DR | P14416 | DRD2 | 217 | No | 0.79 | 539 | 65 | M. Rec |
| | 5HTR1A | P08908 | HTR1A | 214 | No | 0.77 | 301 | 76 | M. Rec |
| | 5HTR1B | P28222 | HTR1B | 1898 | Yes | 0.77 | 310 | 86 | M. Rec |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| | D(4)DR | P21917 | DRD4 | 219 | No | 0.75 | 274 | 15 | M. Rec |
| | D(3)DR | P35462 | DRD3 | 234 | No | 0.75 | 324 | 36 | M. Rec |
| | 5HTR2A | P28223 | HTR2A | 224 | No | 0.75 | 269 | 29 | M. Rec |
| | 5HTR2C | P28335 | HTR2C | 225 | No | 0.75 | 205 | 18 | M. Rec |
| | HH1R | P35367 | HRH1 | 231 | No | 0.75 | 99 | 5 | M. Rec |
| | 5HTR2B | P41595 | HTR2B | 1833 | No | 0.75 | 205 | 18 | M. Rec |
| | B2AR | P07550 | ADRB2 | 210 | No | 0.75 | 473 | 7 | M. Rec |
| | B1AR | P08588 | ADRB1 | 213 | No | 0.75 | 475 | 7 | M. Rec |
| | B3AR | P13945 | ADRB3 | 246 | No | 0.75 | 455 | 7 | M. Rec |
| | D(1A)DR | P21728 | DRD1 | 2056 | No | 0.75 | 38 | 18 | M. Rec |
| | D(1B)DR | P21918 | DRD5 | 1850 | No | 0.75 | 33 | 18 | M. Rec |
| | 5HTR1D | P28221 | HTR1D | 1983 | No | 0.75 | 100 | 77 | M. Rec |
| 009 | 5HTR2A | P28223 | HTR2A | 224 | No | 0.83 | 773 | 28 | M. Rec |
| | D(2)DR | P14416 | DRD2 | 217 | No | 0.83 | 1942 | 74 | M. Rec |
| | D(4)DR | P21917 | DRD4 | 219 | No | 0.83 | 721 | 18 | M. Rec |
| | D(3)DR | P35462 | DRD3 | 234 | No | 0.83 | 1145 | 38 | M. Rec |
| | 5HTR1A | P08908 | HTR1A | 214 | No | 0.8 | 1076 | 68 | M. Rec |
| | 5HTR1B | P28222 | HTR1B | 1898 | Yes | 0.8 | 1130 | 76 | M. Rec |
| | 5HTR1D | P28221 | HTR1D | 1983 | No | 0.8 | 407 | 65 | M. Rec |
| | 5HTR2C | P28335 | HTR2C | 225 | No | 0.8 | 478 | 16 | M. Rec |
| | 5HTR1E | P28566 | HTR1E | 2182 | No | 0.8 | 335 | 54 | M. Rec |
| | 5HTR1F | P30939 | HTR1F | 1805 | No | 0.8 | 335 | 54 | M. Rec |
| | 5HTR7 | P34969 | HTR7 | 3155 | No | 0.8 | 310 | 14 | M. Rec |
| | 5HTR2B | P41595 | HTR2B | 1833 | No | 0.8 | 478 | 16 | M. Rec |
| | 5HTR6 | P50406 | HTR6 | 3371 | No | 0.8 | 568 | 69 | M. Rec |
| | 5HTR5A | P47898 | HTR5A | 3426 | No | 0.8 | 52 | 10 | M. Rec |
| | D(1A)DR | P21728 | DRD1 | 2056 | No | 0.78 | 191 | 18 | M. Rec |
| 010 | 5HTR6 | P50406 | HTR6 | 3371 | No | 0.82 | 383 | 55 | M. Rec |
| | D(4)DR | P21917 | DRD4 | 219 | No | 0.82 | 950 | 16 | M. Rec |
| | D(2)DR | P14416 | DRD2 | 217 | No | 0.8 | 2423 | 73 | M. Rec |
| | 5HTR1D | P28221 | HTR1D | 1983 | No | 0.8 | 487 | 74 | M. Rec |
| | 5HTR1B | P28222 | HTR1B | 1898 | Yes | 0.8 | 1283 | 86 | M. Rec |
| | 5HTR2A | P28223 | HTR2A | 224 | No | 0.8 | 959 | 32 | M. Rec |
| | 5HTR7 | P34969 | HTR7 | 3155 | No | 0.8 | 465 | 14 | M. Rec |
| | 5HTR1A | P08908 | HTR1A | 214 | No | 0.8 | 1246 | 76 | M. Rec |
| | D(1A)DR | P21728 | DRD1 | 2056 | No | 0.8 | 189 | 19 | M. Rec |
| | D(1B)DR | P21918 | DRD5 | 1850 | No | 0.8 | 145 | 19 | M. Rec |
| | 5HTR2C | P28335 | HTR2C | 225 | No | 0.8 | 575 | 21 | M. Rec |
| | D(3)DR | P35462 | DRD3 | 234 | No | 0.8 | 1516 | 37 | M. Rec |
| | 5HTR2B | P41595 | HTR2B | 1833 | No | 0.8 | 575 | 21 | M. Rec |
| | 5HTR1E | P28566 | HTR1E | 2182 | No | 0.79 | 419 | 60 | M. Rec |
| | 5HTR1F | P30939 | HTR1F | 1805 | Yes | 0.79 | 419 | 60 | M. Rec |
| 011 | 5HTR1A | P08908 | HTR1A | 214 | No | 0.91 | 1137 | 78 | M. Rec |
| | 5HTR1B | P28222 | HTR1B | 1898 | Yes | 0.91 | 1194 | 88 | M. Rec |
| | 5HTR6 | P50406 | HTR6 | 3371 | No | 0.9 | 361 | 44 | M. Rec |
| | D(2)DR | P14416 | DRD2 | 217 | No | 0.9 | 2285 | 86 | M. Rec |
| | D(3)DR | P35462 | DRD3 | 234 | No | 0.9 | 1325 | 36 | M. Rec |
| | D(4)DR | P21917 | DRD4 | 219 | No | 0.89 | 823 | 16 | M. Rec |
| | 5HTR2A | P28223 | HTR2A | 224 | No | 0.89 | 803 | 30 | M. Rec |
| | D(1A)DR | P21728 | DRD1 | 2056 | No | 0.89 | 239 | 19 | M. Rec |
| | D(1B)DR | P21918 | DRD5 | 1850 | No | 0.89 | 181 | 19 | M. Rec |
| | 5HTR2C | P28335 | HTR2C | 225 | Yes | 0.88 | 469 | 19 | M. Rec |
| | 5HTR2B | P41595 | HTR2B | 1833 | No | 0.88 | 469 | 19 | M. Rec |
| | A2aAR | P08913 | ADRA2A | 1867 | No | 0.88 | 54 | 9 | M. Rec |
| | A2BAR | P18089 | ADRA2B | 1942 | Yes | 0.88 | 55 | 9 | M. Rec |
| | A2CAR | P18825 | ADRA2C | 1916 | No | 0.88 | 54 | 9 | M. Rec |
| | CXCCRT3 | P49682 | CXCR3 | 4441 | No | 0.86 | 90 | 63 | M. Rec |
| 012 | 5HTR6 | P50406 | HTR6 | 3371 | No | 0.84 | 483 | 39 | M. Rec |
| | 5HTR1A | P08908 | HTR1A | 214 | No | 0.83 | 1292 | 68 | M. Rec |
| | 5HTR1D | P28221 | HTR1D | 1983 | No | 0.83 | 522 | 69 | M. Rec |
| | 5HTR1B | P28222 | HTR1B | 1898 | No | 0.83 | 1337 | 77 | M. Rec |
| | 5HTR1E | P28566 | HTR1E | 2182 | No | 0.83 | 441 | 57 | M. Rec |
| | 5HTR1F | P30939 | HTR1F | 1805 | Yes | 0.83 | 441 | 57 | M. Rec |
| | 5HTR2A | P28223 | HTR2A | 224 | No | 0.8 | 936 | 29 | M. Rec |
| | D(2)DR | P14416 | DRD2 | 217 | No | 0.78 | 2317 | 74 | M. Rec |
| | D(4)DR | P21917 | DRD4 | 219 | No | 0.78 | 909 | 15 | M. Rec |
| | D(3)DR | P35462 | DRD3 | 234 | No | 0.78 | 1434 | 36 | M. Rec |
| | 5HTR2C | P28335 | HTR2C | 225 | No | 0.78 | 563 | 18 | M. Rec |
| | 5HTR7 | P34969 | HTR7 | 3155 | No | 0.78 | 472 | 12 | M. Rec |
| | 5HTR2B | P41595 | HTR2B | 1833 | No | 0.78 | 563 | 18 | M. Rec |
| | D(1A)DR | P21728 | DRD1 | 2056 | No | 0.78 | 173 | 18 | M. Rec |
| | D(1B)DR | P21918 | DRD5 | 1850 | No | 0.78 | 128 | 18 | M. Rec |
| 013 | D(2)DR | P14416 | DRD2 | 217 | No | 0.9 | 430 | 95 | M. Rec |
| | D(1A)DR | P21728 | DRD1 | 2056 | No | 0.9 | 36 | 20 | M. Rec |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| | D(4)DR | P21917 | DRD4 | 219 | No | 0.9 | 235 | 17 | M. Rec |
| | D(1B)DR | P21918 | DRD5 | 1850 | No | 0.9 | 32 | 20 | M. Rec |
| | 5HTR1D | P28221 | HTR1D | 1983 | No | 0.9 | 90 | 84 | M. Rec |
| | 5HTR1B | P28222 | HTR1B | 1898 | Yes | 0.9 | 274 | 111 | M. Rec |
| | 5HTR2A | P28223 | HTR2A | 224 | No | 0.9 | 207 | 33 | M. Rec |
| | 5HTR2C | P28335 | HTR2C | 225 | No | 0.9 | 150 | 22 | M. Rec |
| | D(3)DR | P35462 | DRD3 | 234 | No | 0.9 | 262 | 38 | M. Rec |
| | 5HTR2B | P41595 | HTR2B | 1833 | No | 0.9 | 150 | 22 | M. Rec |
| | 5HTR6 | P50406 | HTR6 | 3371 | No | 0.9 | 46 | 57 | M. Rec |
| | 5HTR7 | P34969 | HTR7 | 3155 | No | 0.89 | 29 | 16 | M. Rec |
| | 5HTR1A | P08908 | HTR1A | 214 | No | 0.88 | 267 | 101 | M. Rec |
| | A2aAR | P08913 | ADRA2A | 1867 | No | 0.88 | 52 | 10 | M. Rec |
| | A2BAR | P18089 | ADRA2B | 1942 | No | 0.88 | 52 | 10 | M. Rec |
| 014 | 5HTR1B | P28222 | HTR1B | 1898 | Yes | 0.75 | 365 | 78 | M. Rec |
| | D(2)DR | P14416 | DRD2 | 217 | No | 0.74 | 631 | 57 | M. Rec |
| | D(1A)DR | P21728 | DRD1 | 2056 | No | 0.74 | 53 | 18 | M. Rec |
| | D(4)DR | P21917 | DRD4 | 219 | Yes | 0.74 | 350 | 15 | M. Rec |
| | D(3)DR | P35462 | DRD3 | 234 | No | 0.74 | 413 | 33 | M. Rec |
| | 5HTR2A | P28223 | HTR2A | 224 | No | 0.74 | 333 | 25 | M. Rec |
| | 5HTR2C | P28335 | HTR2C | 225 | No | 0.74 | 259 | 14 | M. Rec |
| | 5HTR2B | P41595 | HTR2B | 1833 | No | 0.74 | 259 | 14 | M. Rec |
| | 5HTR6 | P50406 | HTR6 | 3371 | No | 0.72 | 78 | 19 | M. Rec |
| | 5HTR1D | P28221 | HTR1D | 1983 | No | 0.72 | 118 | 61 | M. Rec |
| | 5HTR1A | P08908 | HTR1A | 214 | No | 0.72 | 358 | 73 | M. Rec |
| | CP4502D6 | P10635 | CYP2D6 | 289 | No | 0.72 | 23 | 2 | Enz |
| | CP4502J2 | P51589 | CYP2J2 | 3491 | No | 0.72 | 23 | 2 | Enz |
| | A2aAR | P08913 | ADRA2A | 1867 | No | 0.72 | 91 | 8 | M. Rec |
| | MAPTau | P10636 | MAPT | 1293224 | No | 0.72 | 348 | 8 | Unc |
| 015 | CP4502D6 | P10635 | CYP2D6 | 289 | No | 0.78 | 22 | 2 | Enz |
| | CP4502J2 | P51589 | CYP2J2 | 3491 | No | 0.78 | 22 | 2 | Enz |
| | MAPTau | P10636 | MAPT | 1293224 | No | 0.77 | 268 | 9 | Unc |
| | D(4)DR | P21917 | DRD4 | 219 | No | 0.77 | 311 | 15 | M. Rec |
| | 5HTR2A | P28223 | HTR2A | 224 | No | 0.77 | 314 | 25 | M. Rec |
| | 5HTR2C | P28335 | HTR2C | 225 | No | 0.77 | 249 | 14 | M. Rec |
| | 5HTR2B | P41595 | HTR2B | 1833 | No | 0.77 | 249 | 14 | M. Rec |
| | MBLP#1 | Q9NR56 | MBNL1 | 1293317 | No | 0.75 | 227 | 3 | Unc |
| | MBLP#2 | Q5VZF2 | MBNL2 | | Yes | 0.75 | 227 | 3 | Unc |
| | MBLP#3 | Q.9NUK0 | MBNL3 | | Yes | 0.75 | 227 | 3 | Unc |
| | 5HTR6 | P50406 | HTR6 | 3371 | No | 0.75 | 82 | 19 | M. Rec |
| | D(2)DR | P14416 | DRD2 | 217 | No | 0.73 | 564 | 57 | M. Rec |
| | D(1A)DR | P21728 | DRD1 | 2056 | No | 0.73 | 49 | 18 | M. Rec |
| | D(1B)DR | P21918 | DRD5 | 1850 | Yes | 0.73 | 42 | 18 | M. Rec |
| | 5HTR1D | P28221 | HTR1D | 1983 | No | 0.73 | 113 | 58 | M. Rec |
| 016 | 5HTR1A | P08908 | HTR1A | 214 | No | 0.8 | 1056 | 43 | M. Rec |
| | 5HTR1D | P28221 | HTR1D | 1983 | No | 0.8 | 385 | 45 | M. Rec |
| | 5HTR1B | P28222 | HTR1B | 1898 | No | 0.8 | 1103 | 50 | M. Rec |
| | 5HTR1E | P28566 | HTR1E | 2182 | No | 0.8 | 314 | 36 | M. Rec |
| | 5HTR1F | P30939 | HTR1F | 1805 | Yes | 0.8 | 314 | 36 | M. Rec |
| | D(2)DR | P14416 | DRD2 | 217 | No | 0.78 | 2111 | 59 | M. Rec |
| | D(1A)DR | P21728 | DRD1 | 2056 | Yes | 0.78 | 129 | 18 | M. Rec |
| | D(4)DR | P21917 | DRD4 | 219 | No | 0.78 | 718 | 15 | M. Rec |
| | D(3)DR | P35462 | DRD3 | 234 | No | 0.78 | 1173 | 34 | M. Rec |
| | 5HTR2A | P28223 | HTR2A | 224 | No | 0.77 | 840 | 26 | M. Rec |
| | 5HTR7 | P34969 | HTR7 | 3155 | No | 0.75 | 367 | 10 | M. Rec |
| | 5HTR2C | P28335 | HTR2C | 225 | No | 0.71 | 515 | 15 | M. Rec |
| | 5HTR2B | P41595 | HTR2B | 1833 | No | 0.71 | 515 | 15 | M. Rec |
| | 5HTR6 | P50406 | HTR6 | 3371 | No | 0.71 | 287 | 35 | M. Rec |
| | D(1B)DR | P21918 | DRD5 | 1850 | No | 0.69 | 83 | 18 | M. Rec |
| 017 | 5HTR1A | P08908 | HTR1A | 214 | No | 0.8 | 735 | 88 | M. Rec |
| | 5HTR1B | P28222 | HTR1B | 1898 | Yes | 0.8 | 781 | 98 | M. Rec |
| | D(2)DR | P14416 | DRD2 | 217 | No | 0.77 | 1408 | 76 | M. Rec |
| | 5HTR2A | P28223 | HTR2A | 224 | No | 0.77 | 563 | 30 | M. Rec |
| | 5HTR2C | P28335 | HTR2C | 225 | No | 0.77 | 342 | 19 | M. Rec |
| | D(3)DR | P35462 | DRD3 | 234 | No | 0.77 | 752 | 37 | M. Rec |
| | 5HTR2B | P41595 | HTR2B | 1833 | No | 0.77 | 342 | 19 | M. Rec |
| | 5HTR6 | P50406 | HTR6 | 3371 | No | 0.75 | 256 | 37 | M. Rec |
| | MAPTau | P10636 | MAPT | 1293224 | No | 0.75 | 398 | 12 | Unc |
| | D(4)DR | P21917 | DRD4 | 219 | No | 0.75 | 469 | 16 | M. Rec |
| | 5HTR1D | P28221 | HTR1D | 1983 | No | 0.75 | 263 | 84 | M. Rec |
| | 5HTR7 | P34969 | HTR7 | 3155 | No | 0.75 | 240 | 13 | M. Rec |
| | 5HTR5A | P47898 | HTR5A | 3426 | No | 0.75 | 23 | 9 | M. Rec |
| | 5HTR1E | P28566 | HTR1E | 2182 | No | 0.75 | 203 | 70 | M. Rec |
| | 5HTR1F | P30939 | HTR1F | 1805 | Yes | 0.75 | 203 | 70 | M. Rec |

-continued

| Compound Number | Target | Uniprot ID | Gene Code | ChEMBL ID | By Homology | Probability | Number of sim. cmpds (3D) | Number of sim. cmpds (2D) | Target Class |
|---|---|---|---|---|---|---|---|---|---|
| 018 | 5HTR2A | P28223 | HTR2A | 224 | Yes | 0.94 | 384 | 39 | M. Rec |
| | D(2)DR | P14416 | DRD2 | 217 | No | 0.94 | 823 | 160 | M. Rec |
| | D(4)DR | P21917 | DRD4 | 219 | No | 0.94 | 340 | 23 | M. Rec |
| | D(3)DR | P35462 | DRD3 | 234 | No | 0.94 | 488 | 80 | M. Rec |
| | D(1A)DR | P21728 | DRD1 | 2056 | No | 0.93 | 77 | 20 | M. Rec |
| | D(1B)DR | P21918 | DRD5 | 1850 | No | 0.93 | 60 | 20 | M. Rec |
| | 5HTR2C | P28335 | HTR2C | 225 | No | 0.92 | 208 | 26 | M. Rec |
| | 5HTR7 | P34969 | HTR7 | 3155 | No | 0.92 | 143 | 21 | M. Rec |
| | 5HTR2B | P41595 | HTR2B | 1833 | No | 0.92 | 208 | 26 | M. Rec |
| | 5HTR1A | P08908 | HTR1A | 214 | No | 0.92 | 420 | 161 | M. Rec |
| | 5HTR1B | P28222 | HTR1B | 1898 | Yes | 0.92 | 442 | 169 | M. Rec |
| | B2AR | P07550 | ADRB2 | 210 | No | 0.92 | 14 | 7 | M. Rec |
| | B1AR | P08588 | ADRB1 | 213 | No | 0.92 | 14 | 7 | M. Rec |
| | B3AR | P13945 | ADRB3 | 246 | Yes | 0.92 | 14 | 7 | M. Rec |
| | 5HTR1D | P28221 | HTR1D | 1983 | No | 0.92 | 179 | 127 | M. Rec |
| 019 | 5HTR2A | P28223 | HTR2A | 224 | No | 0.93 | 635 | 36 | M. Rec |
| | D(2)DR | P14416 | DRD2 | 217 | No | 0.92 | 1559 | 132 | M. Rec |
| | 5HTR2C | P28335 | HTR2C | 225 | No | 0.92 | 392 | 24 | M. Rec |
| | 5HTR7 | P34969 | HTR7 | 3155 | No | 0.92 | 228 | 19 | M. Rec |
| | 5HTR2B | P41595 | HTR2B | 1833 | No | 0.92 | 392 | 24 | M. Rec |
| | B2AR | P07550 | ADRB2 | 210 | No | 0.91 | 18 | 7 | M. Rec |
| | B1 AR | P08588 | ADRB1 | 213 | No | 0.91 | 19 | 7 | M. Rec |
| | 5HTR1A | P08908 | HTR1A | 214 | No | 0.91 | 801 | 133 | M. Rec |
| | B3AR | P13945 | ADRB3 | 246 | Yes | 0.91 | 18 | 7 | M. Rec |
| | D(1A)DR | P21728 | DRD1 | 2056 | No | 0.91 | 194 | 20 | M. Rec |
| | D(4)DR | P21917 | DRD4 | 219 | No | 0.91 | 632 | 23 | M. Rec |
| | D(1B)DR | P21918 | DRD5 | 1850 | No | 0.91 | 160 | 20 | M. Rec |
| | 5HTR1D | P28221 | HTR1D | 1983 | No | 0.91 | 315 | 101 | M. Rec |
| | 5HTR1B | P28222 | HTR1B | 1898 | Yes | 0.91 | 841 | 141 | M. Rec |
| | HH1R | P35367 | HRH1 | 231 | No | 0.91 | 132 | 6 | M. Rec |

Synthetic Routes

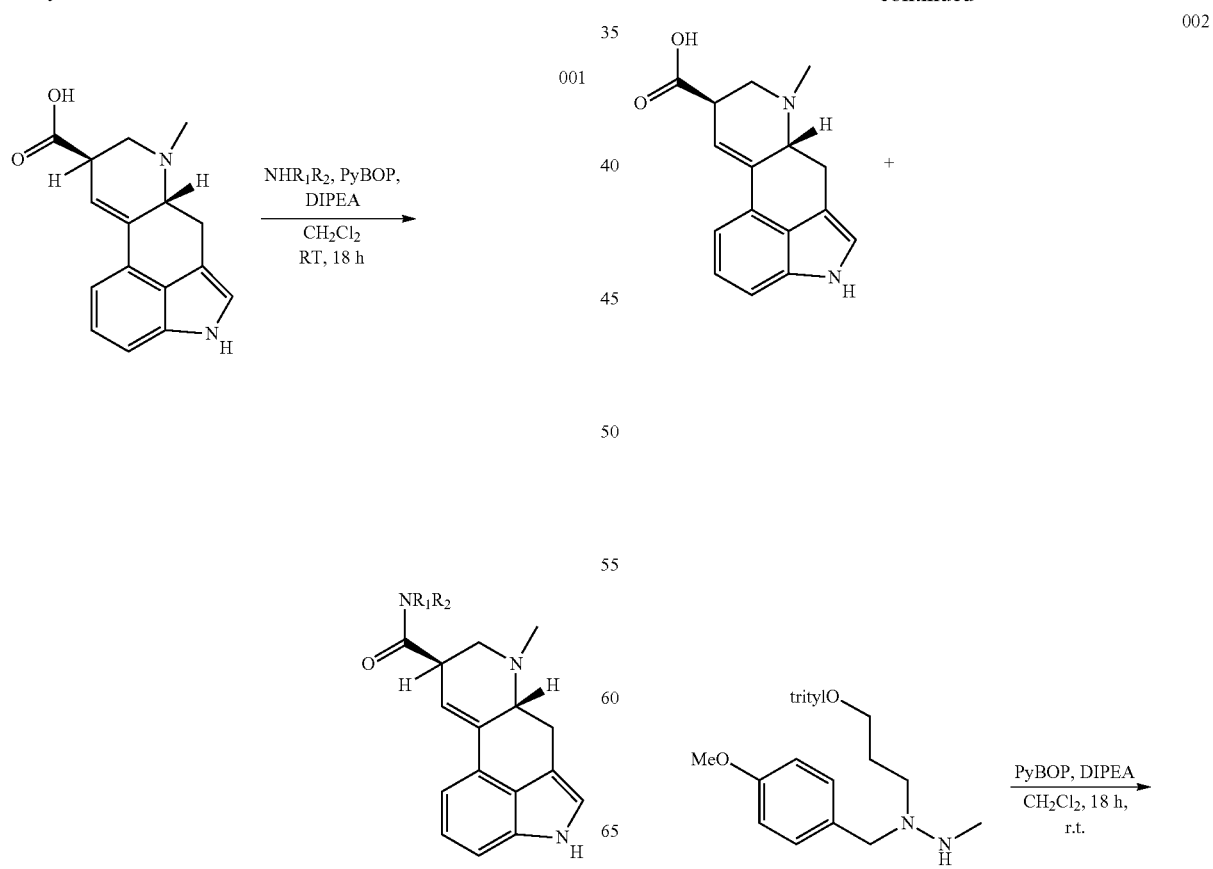

31
-continued
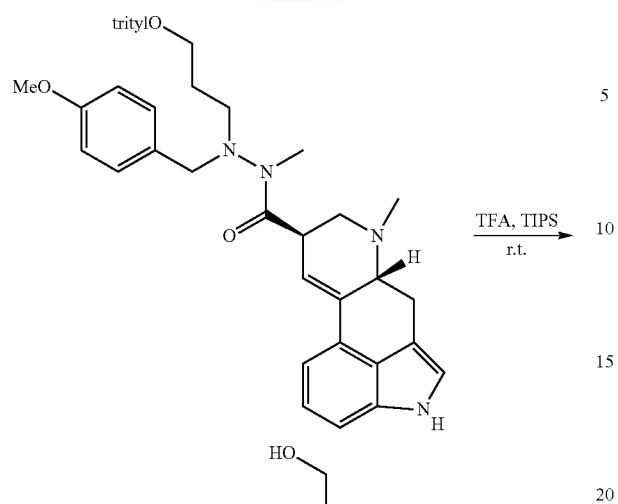
32
-continued
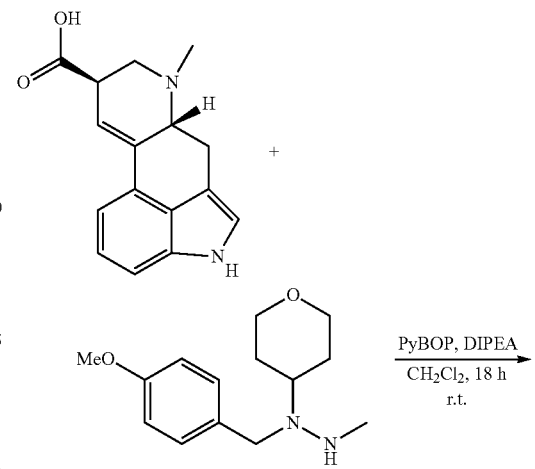
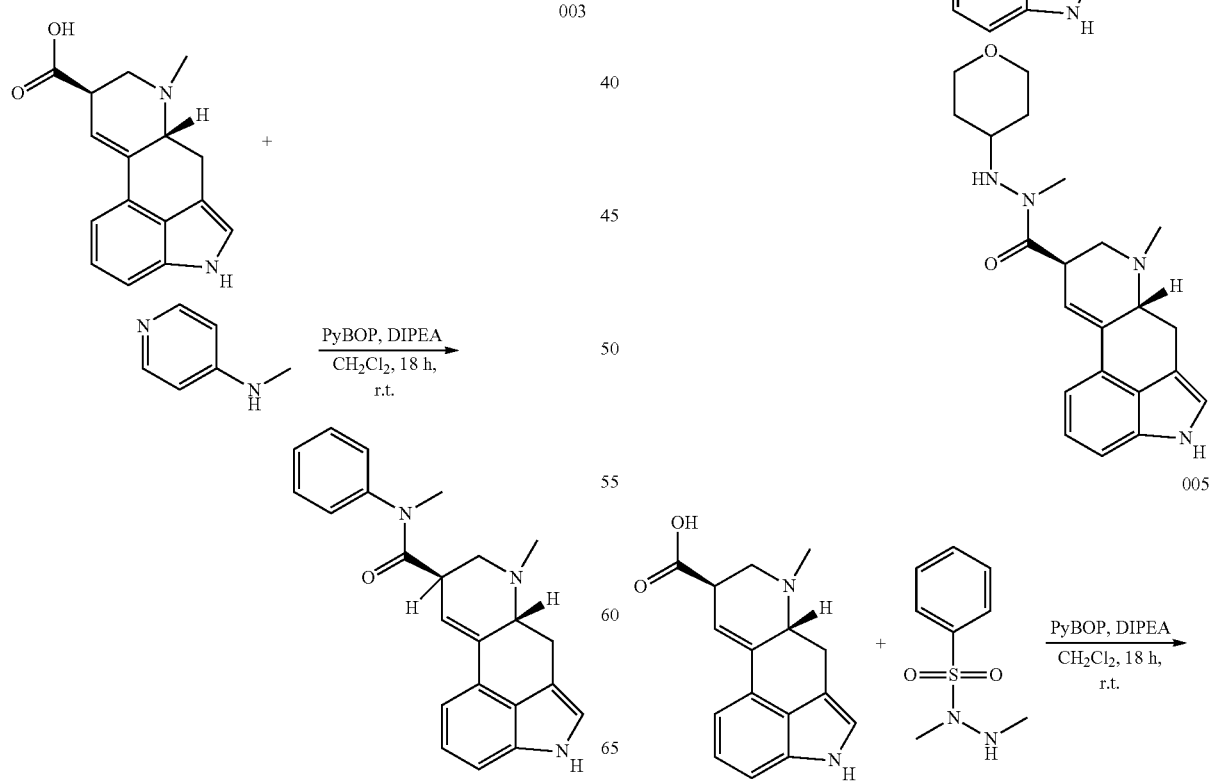

33
-continued
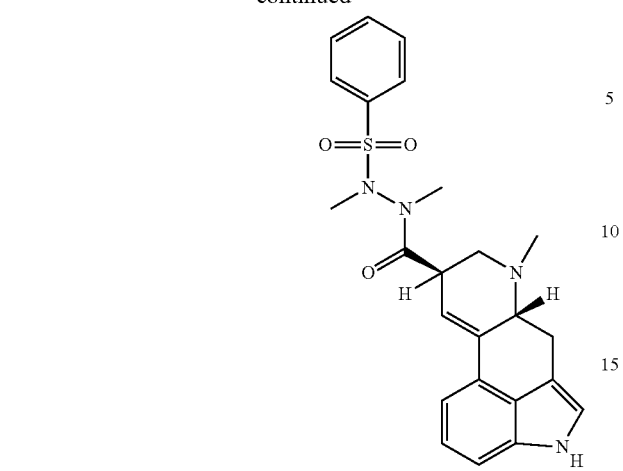
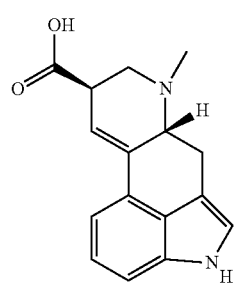
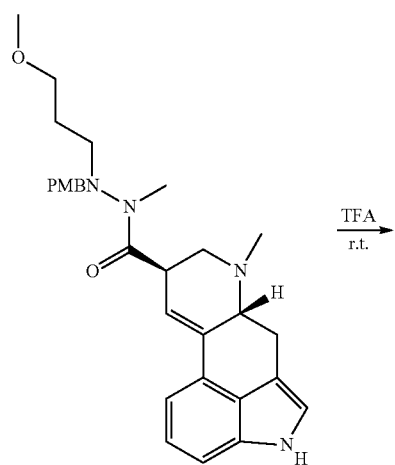
34
-continued
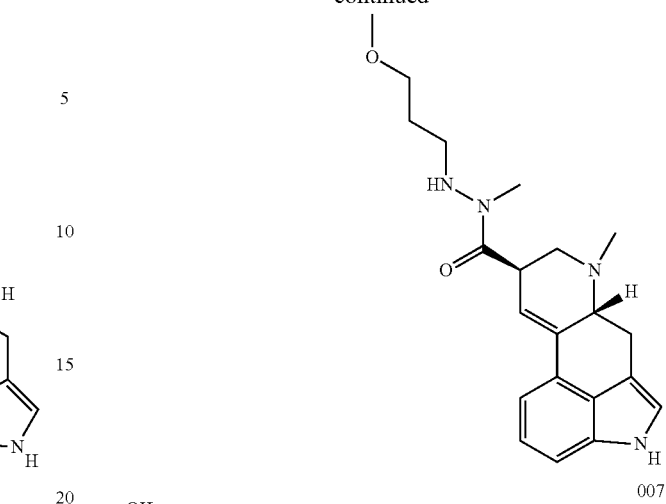
007
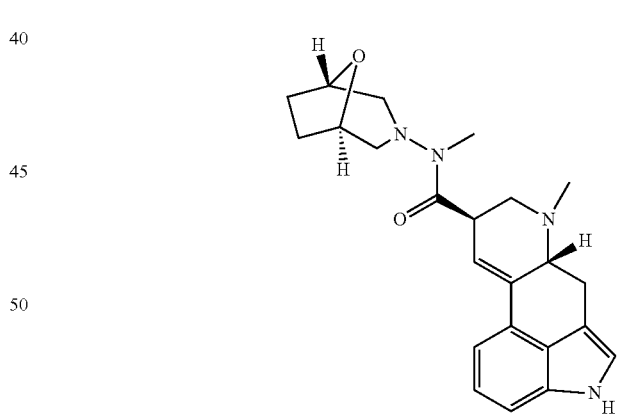
008
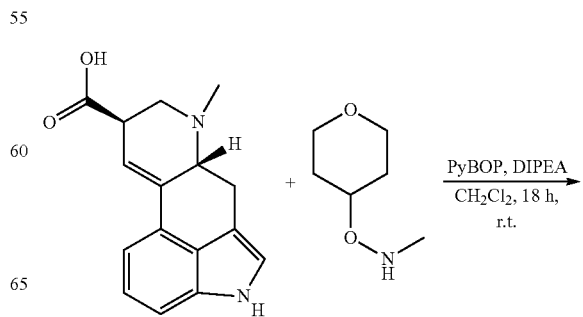

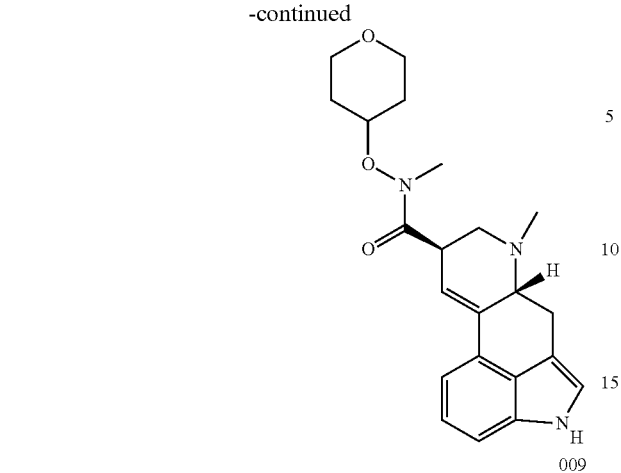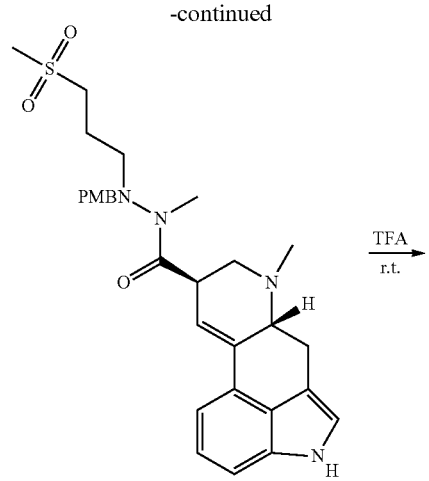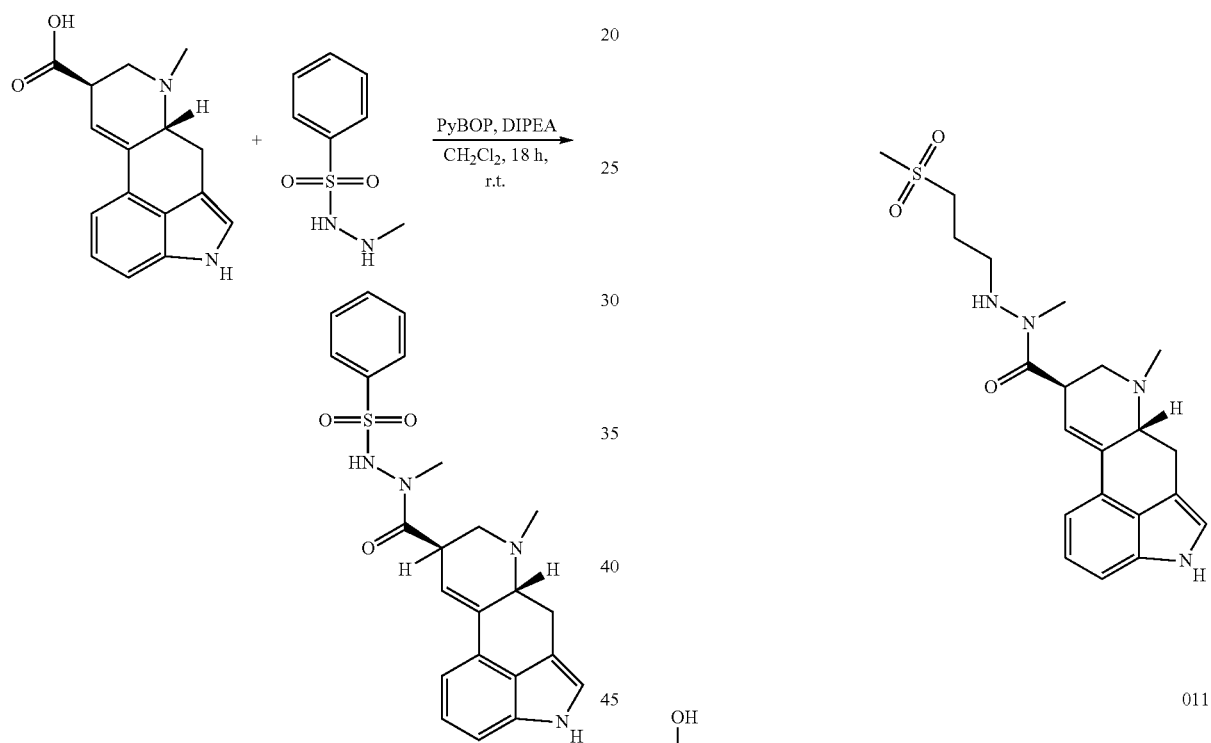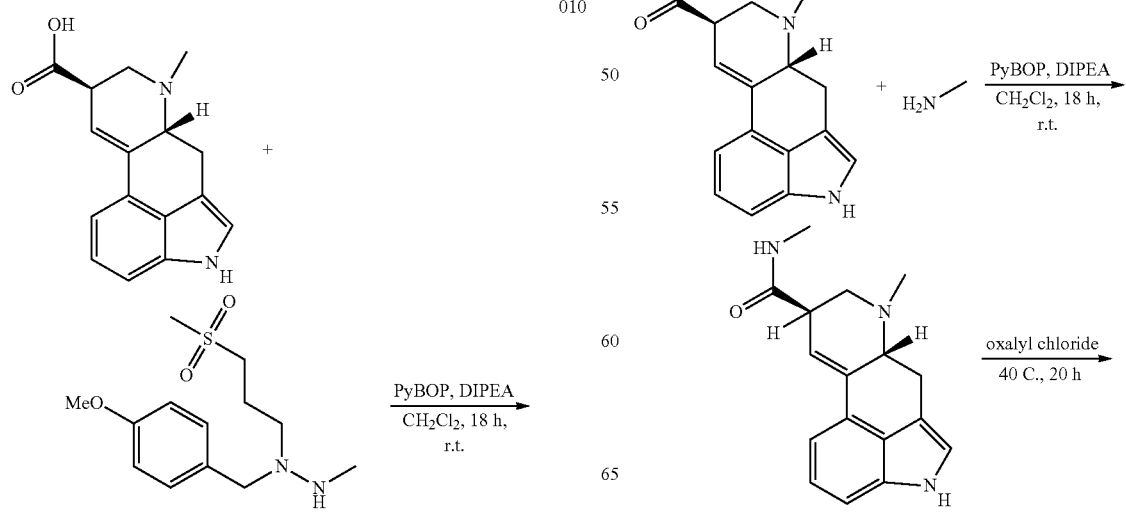

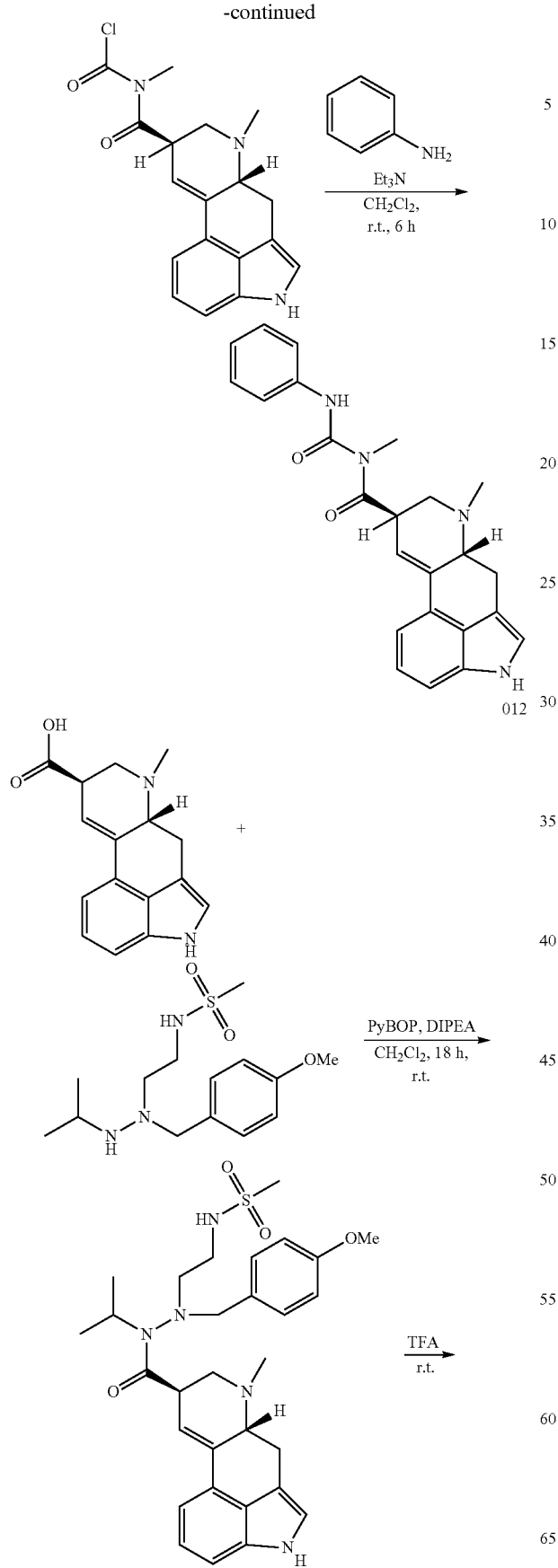
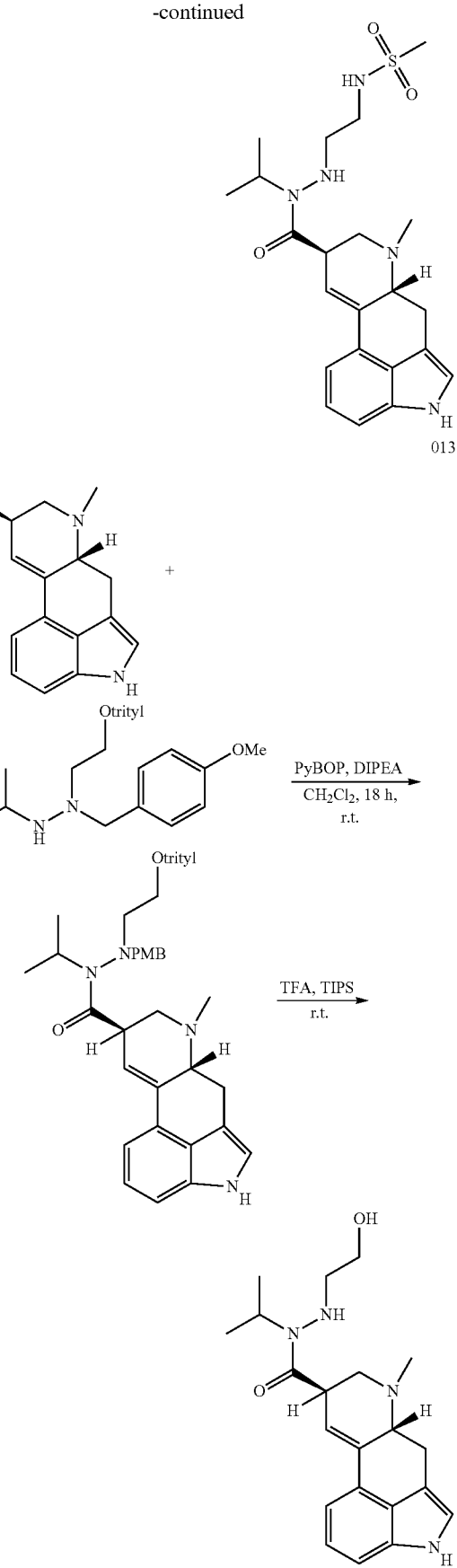

39
-continued
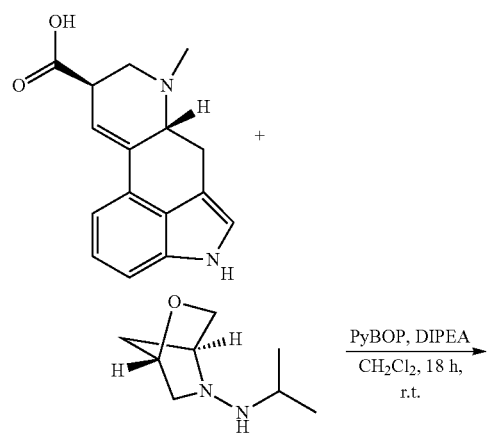
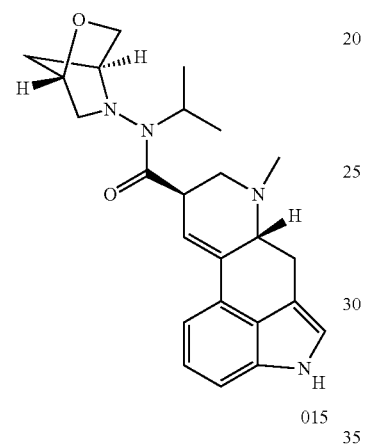
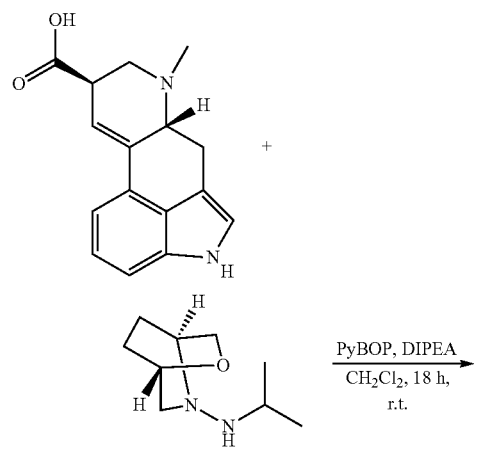
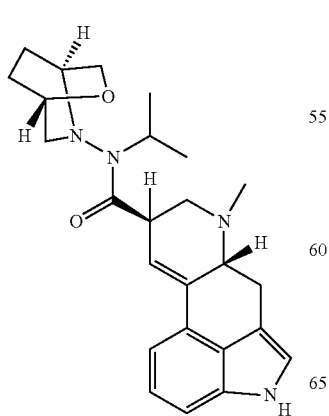
40
-continued
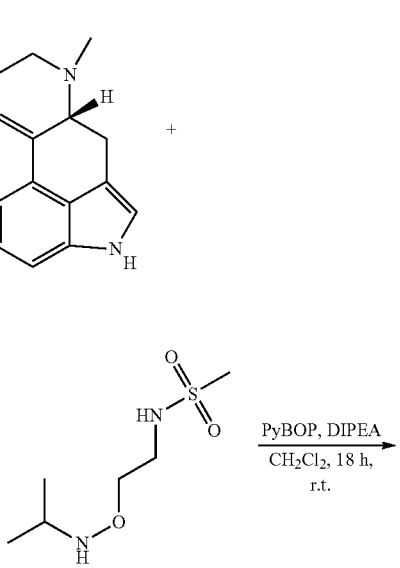
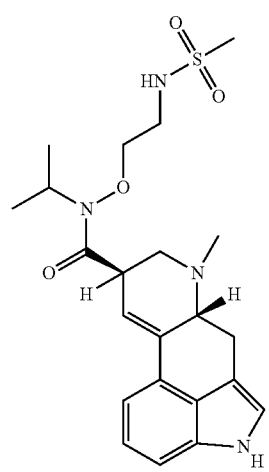
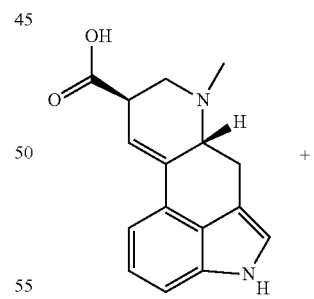
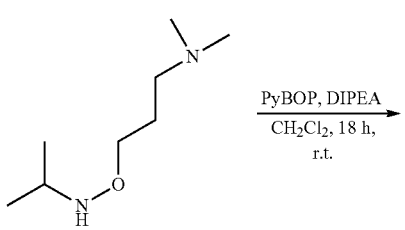

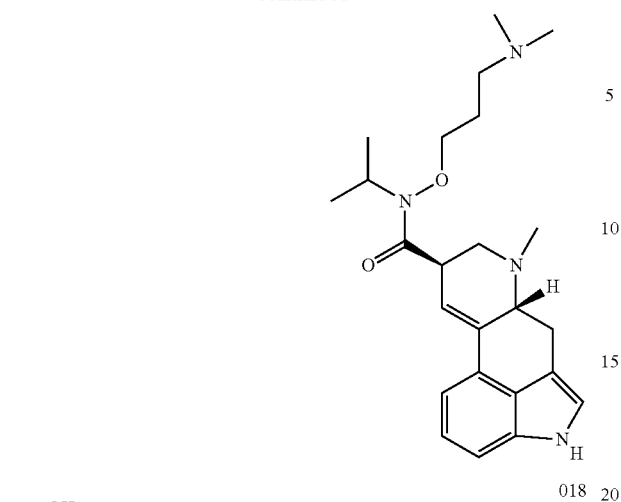

018

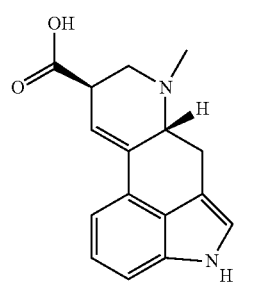

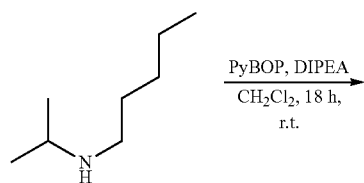
PyBOP, DIPEA
CH₂Cl₂, 18 h, r.t.

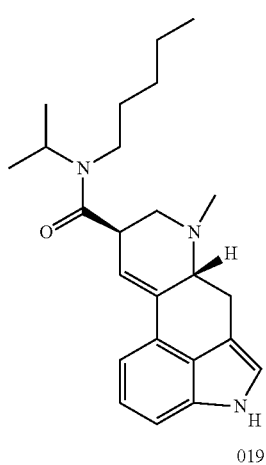

019

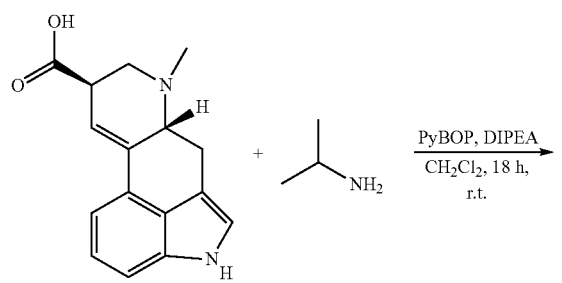
PyBOP, DIPEA
CH₂Cl₂, 18 h, r.t.

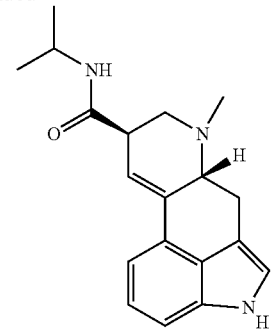

Salt formation is undertaken thereafter in the above routes as necessary, e.g. to give the benzoate, fumarate, citrate, acetate, succinate, halide, fluoride, chloride, bromide, iodide, oxalate, or triflate salt. For example, the addition of hydrogen chloride would provide the chloride salt and benzoic acid would give the benzoate salt.

In an embodiment, there is provided a method of synthesis of any of the herein described compounds. In an embodiment, there is provided a method of synthesis of compound 001, 002, 003, 004, 005, 006, 007, 008, 009, 010, 011, 012, 013, 014, 015, 016, 017, 018 or 019 as herein disclosed.

Further Characterisation of Compounds 018 and 019

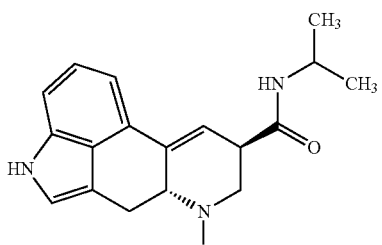

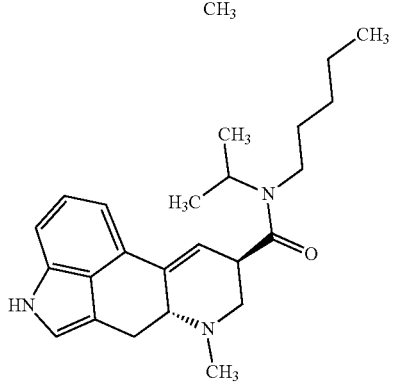

cAMP

Compounds 018 (above, left) and 019 (above, right) were assayed using a serotonin (1a, 1b, 2a, 2c and 7 receptors) cAMP assay, provided by Multispan. The reference used was 10 μM forskolin (a cAMP activator) to calculate the percentage relative response, serotonin was used as the control. The results can be seen in FIG. 1. Compound 019 was active against in all other receptor assays. The results indicate that compound 019 stimulates the $5HT_{2a}R$ leading to downstream activation of cAMP, although the curve response seems atypical compared to the serotonin control.

IP$_1$

Figure 2:
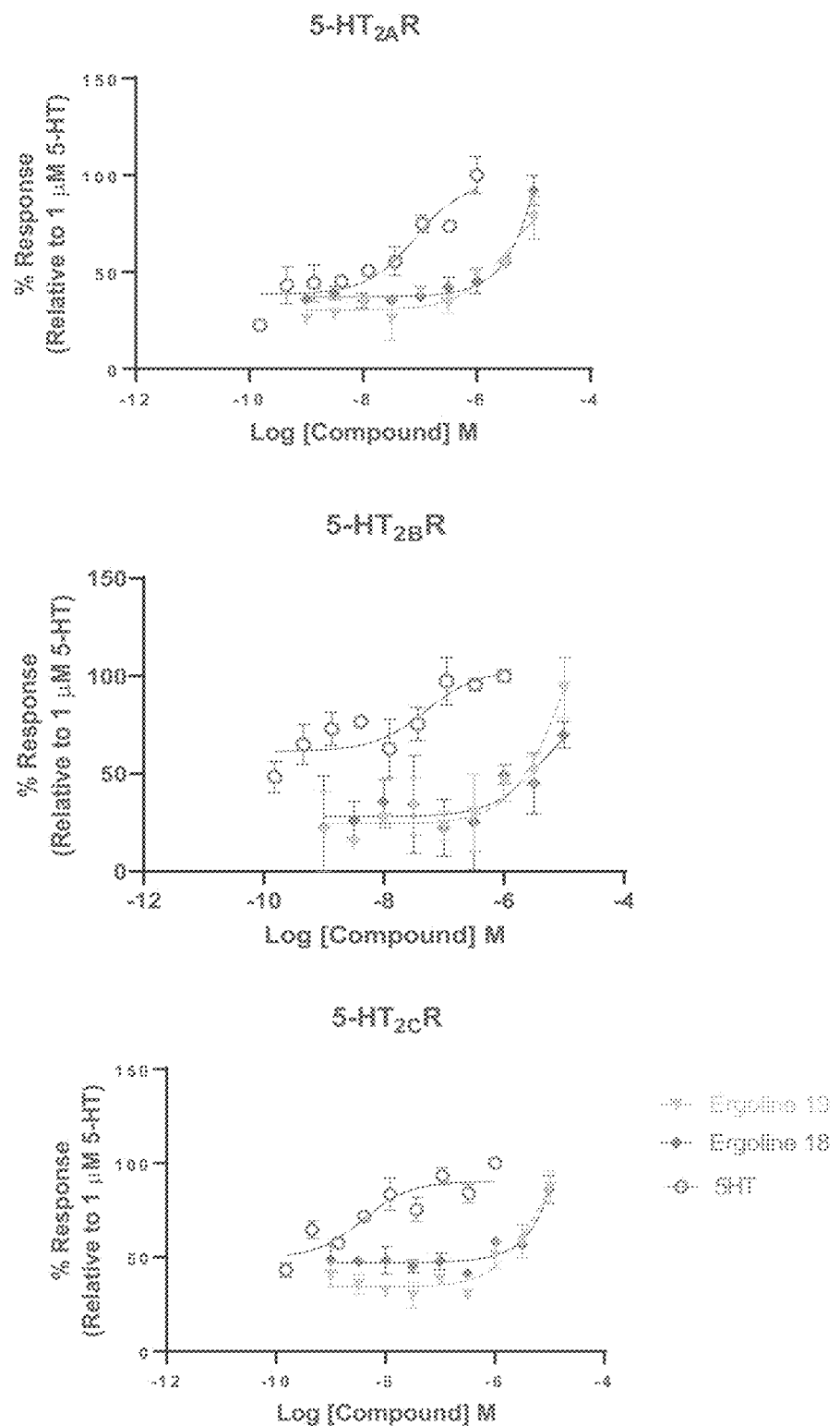
FIG. 2 shows serotonin (2a, 2b and 2c receptors) inositol phosphate 1 ($IP_1$) assay results for compounds 018 and 019.

Compounds 018 and 019 were assayed using a serotonin (2a, 2b and 2c receptors) inositol phosphate 1(IP$_1$) assay, provided by Multispan. The reference used was 1 µM serotonin to calculate the percentage relative response. The results can be seen in FIG. 2. Both compounds appear to some activity against all three target receptors in this assay. This may imply that the compounds do not activate any Gagni pathway.

Ca$^{2+}$

Figure 3:
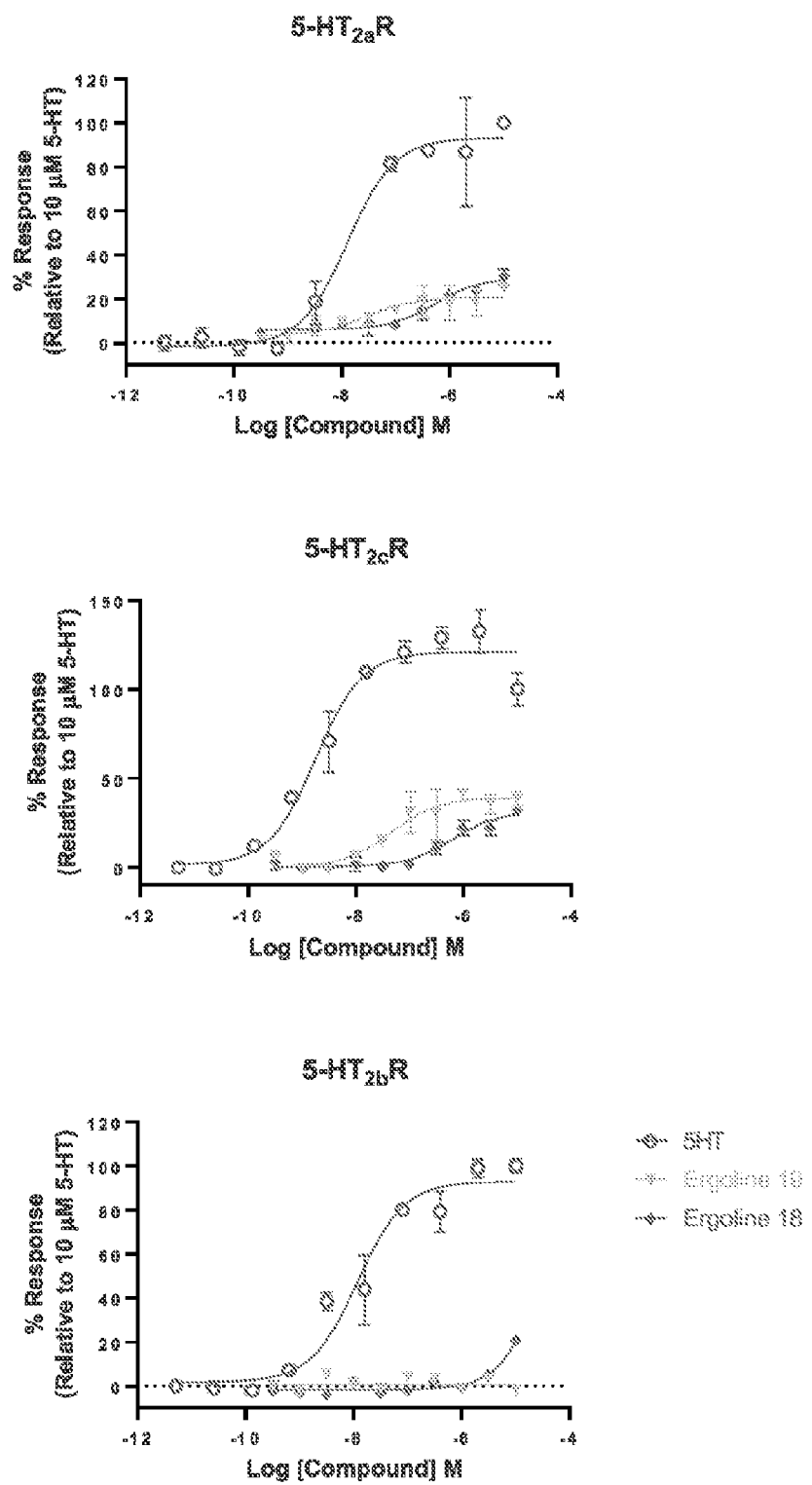
FIG. 3 shows serotonin (2a, 2b and 2c receptors) calcium ($Ca^{2+}$) assay results for compounds 018 and 019.

Compounds 018 and 019 were assayed using a serotonin (2a, 2b and 2c receptors) calcium (Ca$^{2+}$) assay, provided by Multispan. The reference used was 10 µM serotonin to calculate the percentage relative response in relative light units (RLU). The results can be seen in FIG. 3. Both compounds have some activity against the 2a and 2c receptors.

B-Arrestin

Figure 4:
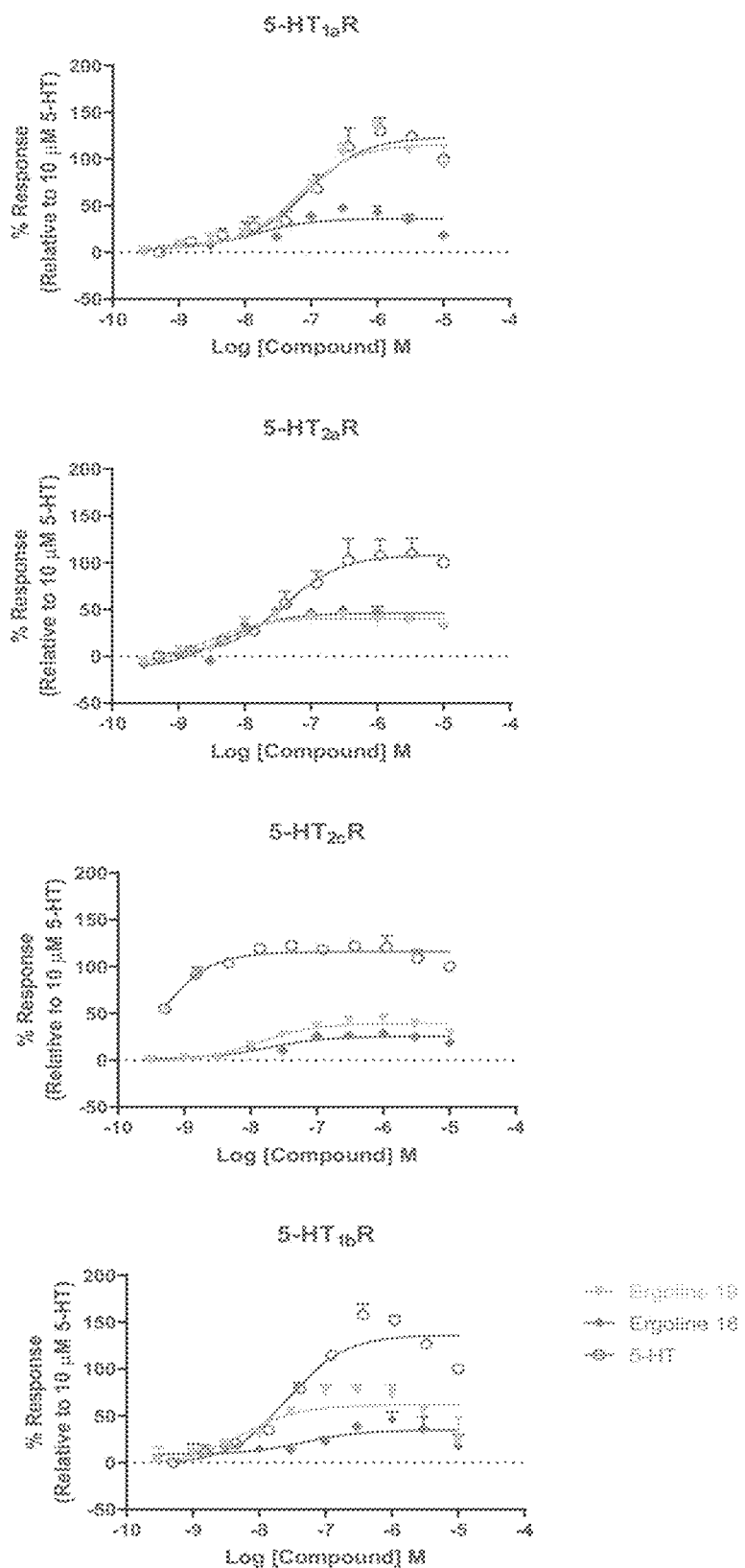
FIG. 4 shows serotonin (1a, 1b, 2a and 2c receptors) B-arrestin assay results for compounds 018 and 019.

Compounds 018 and 019 were assayed using a serotonin (1a, 1b, 2a and 2c receptors) B-arrestin assay, provided by DiscoverX. The reference used was 10 µM serotonin to calculate the percentage relative response. The results can be seen in FIG. 4. In general, both compounds exhibited some activity in comparison to serotonin.

Figure 5:
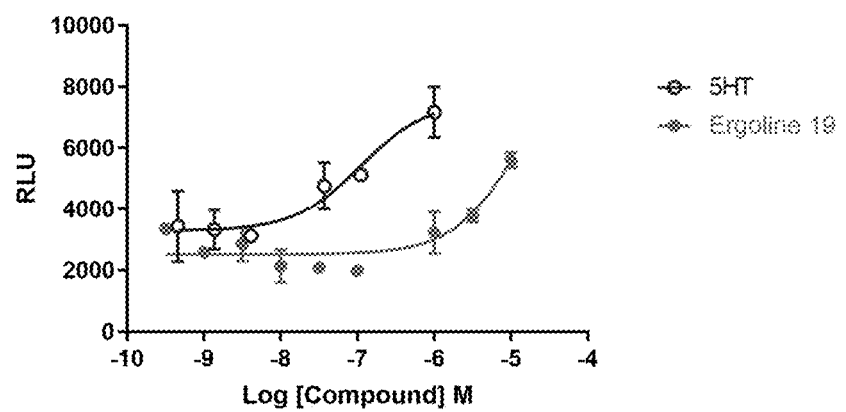
FIG. 5 shows serotonin 2b receptor B-arrestin assay results for compounds 018 and 019.
Figure 5:
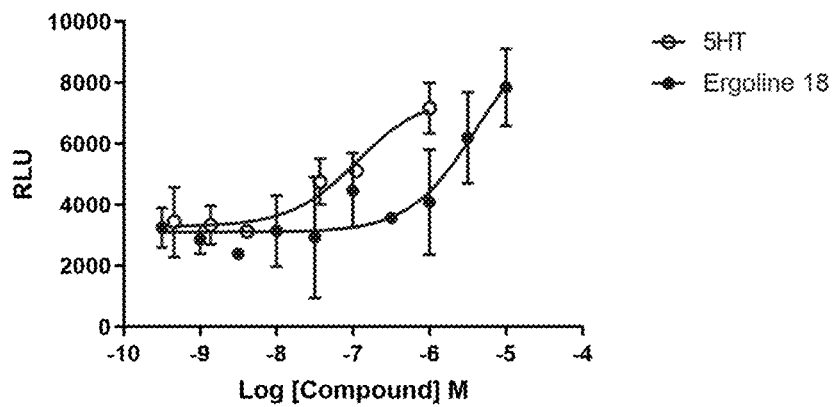

The compounds were also assayed in a serotonin 2b receptor B-arrestin assay, the results of which can be seen in FIG. 5.

Reagent Information

B-Arrestin:

HTR1A PathHunter® eXpress HTR1A CHO-K1 β-Arrestin GPCR Assay 93-0696E2CP0M 200 dp (2×96-well)

HTR1B PathHunter® eXpress HTR1B U2OS β-Arrestin GPCR Assay 93-0697E3CP6M 200 dp (2×96-well)

HTR2A PathHunter® eXpress HTR2A U2OS β-Arrestin GPCR Assay 93-0401E3CP19M 200 dp (2×96-well)

HTR2C PathHunter® eXpress HTR2C U2OS β-Arrestin GPCR Assay 93-0289E3CP3M 200 dp (2×96-well)

Multispan β-arrestin assay with CHO-K1-5HT$_{2b}$R cells—Catalog C1350-1a

Homogeneous Time Resolved Fluorescence (HTRF) and Calcium:

IP-One Gq kit—cisbio—cat. No. 62IPAPEB cAMP Gs dynamic kit—cisbio—cat. No. 62AM4PEC FLIPR calcium 6 assay explorer kit—VWR—cat. No. MLDVR8190

Cells Used in HTRF and Calcium Assays:

MULTISCREEN™ HEK293T Cell Line Stably Expressing Human 5-HT1A Receptor, Catalog DC1319a MULTISCREEN™ HEK293T Cell Line Stably Expressing Human 5-HT1B Receptor, Catalog DC1320a MULTISCREEN™ HEK293T Cell Line Stably Expressing Human 5HT1B Receptor, Catalog DC1320a MULTISCREEN™ CHO-K1 Cell Line Stably Expressing Human 5-HT2A Receptor, Catalog DC1324-1

MULTISCREEN™ CHO-K1 Cell Line Stably Expressing Human 5-HT2B Receptor, Catalog DC1325-1

MULTISCREEN™ CHO-K1 Cell Line Stably Expressing Human 5-HT2C Receptor, Catalog DC1326-1

MULTISCREEN™ HEK293T Cell Line Stably Expressing Human 5-HT7 Receptor, Catalog DC1334

For the B-arrestin assays the cells came with the kits apart from the 2b receptor assay (Valiscreen serotonin 5HT-2B (human) cell line—ES-314-C, Perkin Elmer).

The invention claimed is:

1. A method of treatment of a subject, comprising administering a compound or pharmaceutically acceptable salt thereof to the subject, wherein the subject has depression, anxiety, or a pain condition, and wherein the compound is selected from:

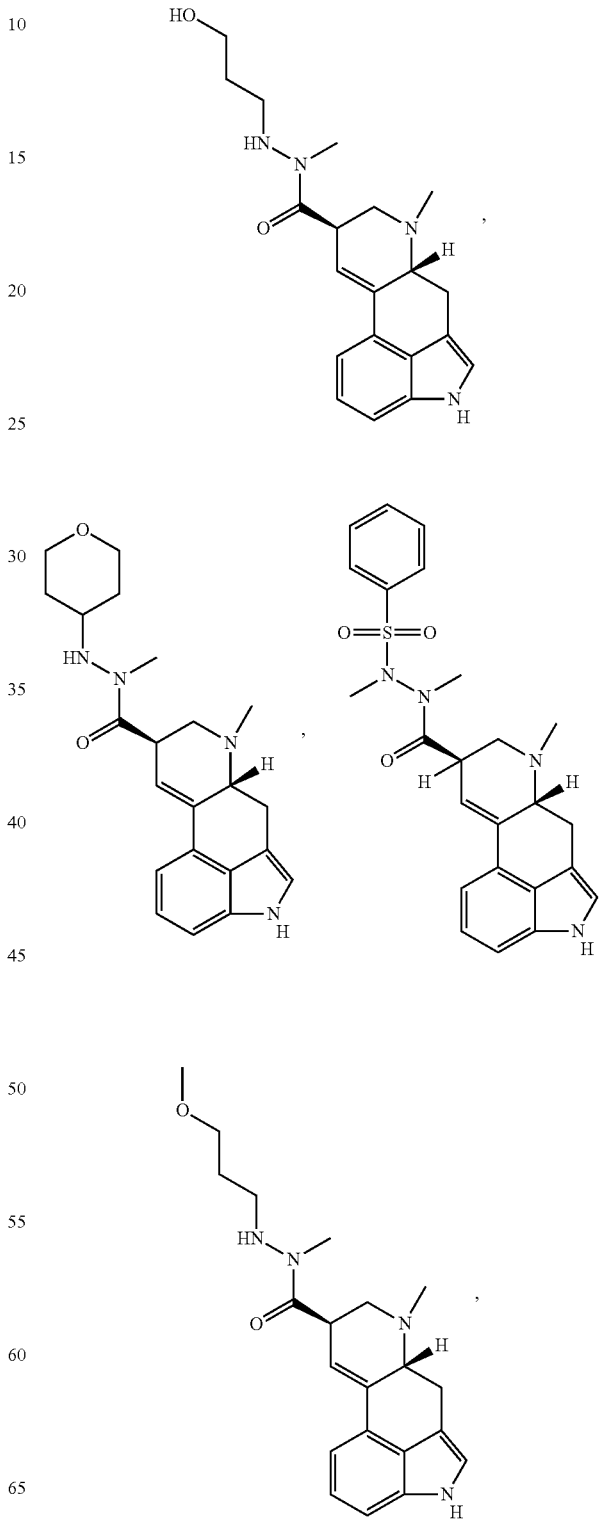

45
-continued
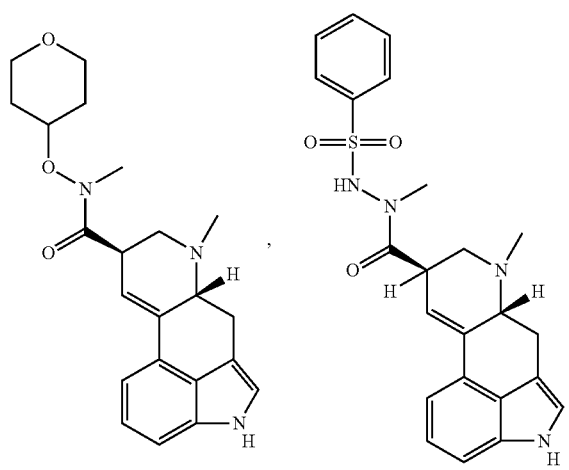
46
-continued
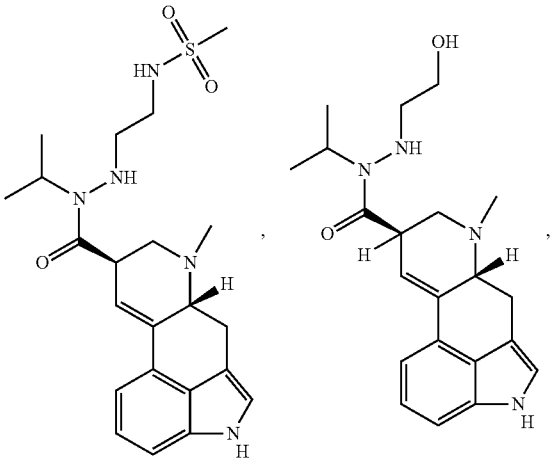
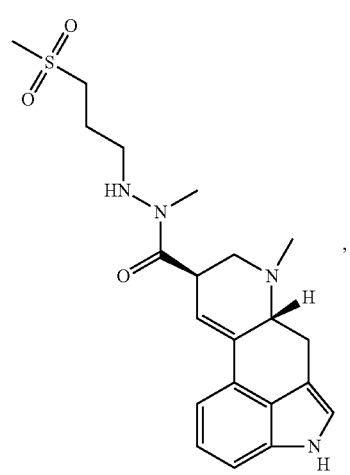
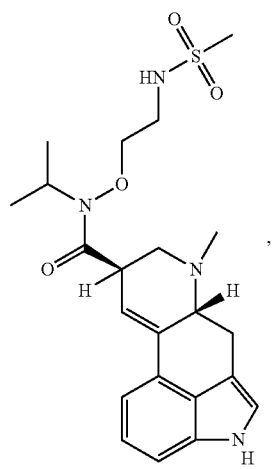
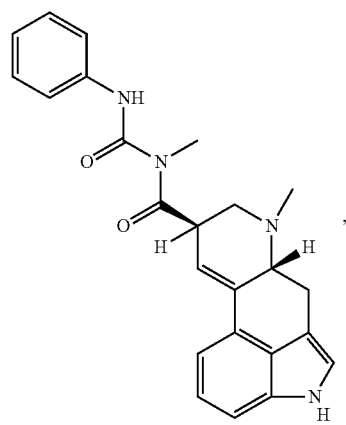
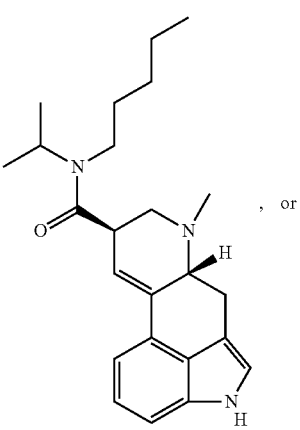, or

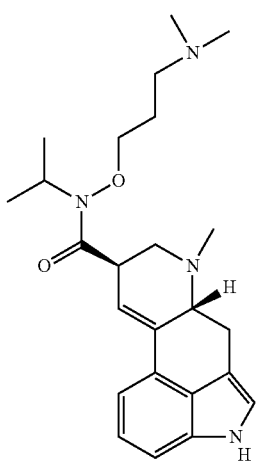

2. The method according to claim 1, wherein the subject is a human.

3. The method according to claim 1, wherein the subject has depression.

4. The method according to claim 3, wherein the subject has treatment-resistant depression.

5. The method according to claim 3, wherein the compound or pharmaceutically acceptable salt thereof is administered together with a complementary treatment, and the complementary treatment is psychotherapy.

6. The method according to claim 1, wherein the subject has anxiety.

7. The method according to claim 1, wherein the subject has a pain condition.

8. The method according to claim 7, wherein the subject has a chronic pain condition.

9. The method according to claim 1, wherein the compound or pharmaceutically acceptable salt thereof is administered one or more times a month.

10. The method according to claim 1, wherein the compound or pharmaceutically acceptable salt thereof is administered orally, buccally, sublingually, transdermally, sublabially, by inhalation, intravenously, or rectally.

11. The method according to claim 1, wherein the compound or pharmaceutically acceptable salt thereof is administered as a composition in a dosage form selected from a tablet, a capsule, granules, powder, an aerosol, an injectable liquid, or a suppository.

12. The method according to claim 1, wherein the compound or pharmaceutically acceptable salt thereof is administered together with a complementary treatment, a further active agent, or both a complementary treatment and a further active agent.

13. A method of treatment of a subject, comprising administering to the subject a composition comprising a pharmaceutically effective amount of a compound or pharmaceutically acceptable salt thereof, wherein the subject has depression, wherein the composition is formulated in a dosage form selected from a tablet, a capsule, granules, powder, an aerosol, and injectable liquid, or a suppository, and wherein the compound is selected from:

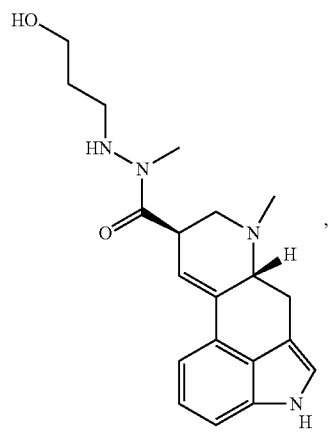

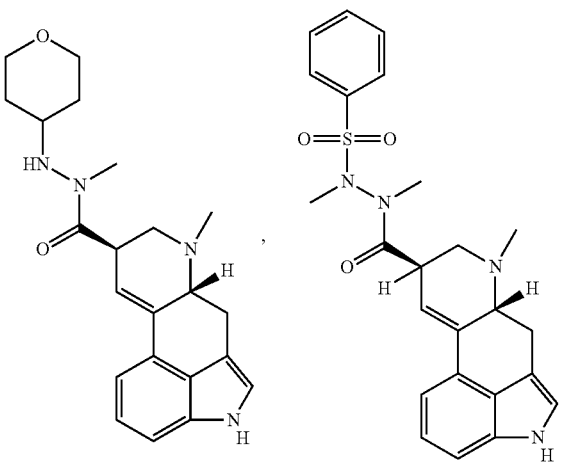

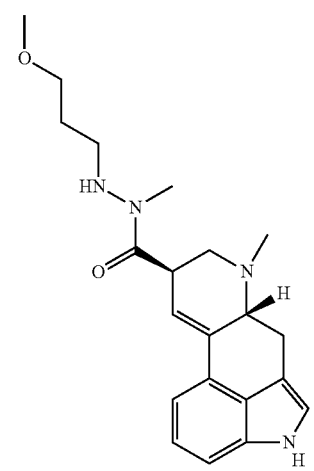

49
-continued
50
-continued
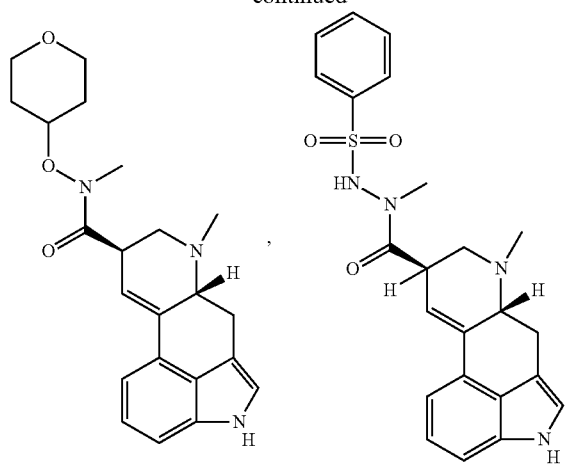
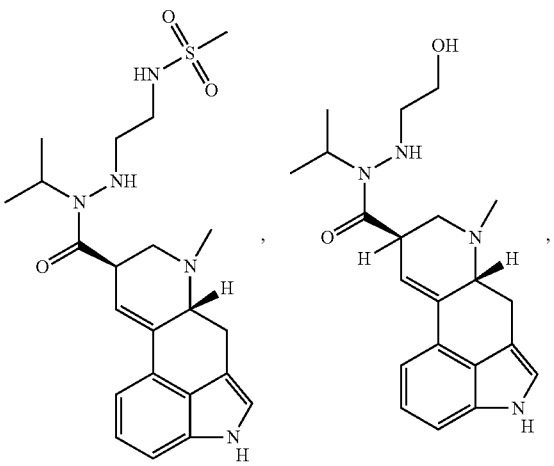
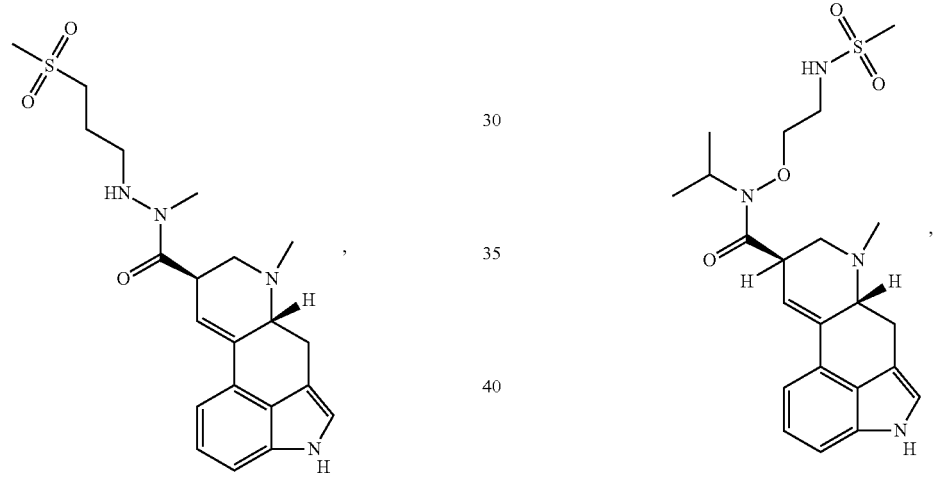
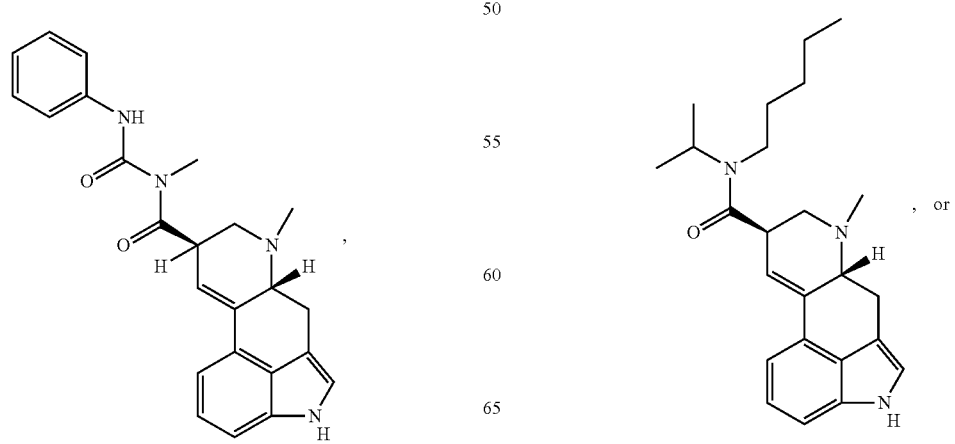

-continued

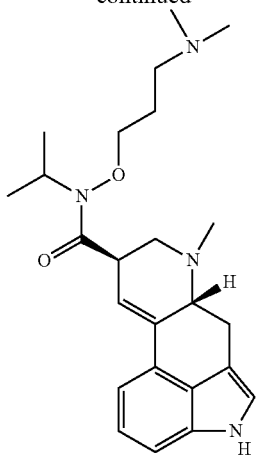

14. The method according to claim 13, wherein the subject has treatment-resistant depression.

15. The method according to claim 13, wherein the composition is administered by inhalation.

16. The method according to claim 13, wherein the composition comprises a dosage amount of the compound or pharmaceutically acceptable salt thereof in the range of 0.05 mg to 100 mg.

17. The method according to claim 13, wherein the composition comprises a dosage amount of the compound or pharmaceutically acceptable salt thereof in the range of 0.1 mg to 50 mg.

18. The method according to claim 13, wherein the composition is administered with a complementary treatment, and the complementary treatment is psychotherapy.

* * * * *

UNITED STATES PATENT AND TRADEMARK OFFICE
CERTIFICATE OF CORRECTION

PATENT NO. : 11,787,806 B2
APPLICATION NO. : 17/932854
DATED : October 17, 2023
INVENTOR(S) : Massimo Muratore et al.

It is certified that error appears in the above-identified patent and that said Letters Patent is hereby corrected as shown below:

In the Claims

In Claim 13, Column 47, Line 66, delete "and injectable" and insert -- an injectable --.

Signed and Sealed this
Twenty-first Day of November, 2023

Katherine Kelly Vidal
Director of the United States Patent and Trademark Office